US007803597B2

(12) United States Patent
Savary et al.

(10) Patent No.: US 7,803,597 B2
(45) Date of Patent: Sep. 28, 2010

(54) THERMALLY-TOLERANT PECTIN METHYLESTERASE

(75) Inventors: Brett J. Savary, Jonesboro, AR (US); Randall G. Cameron, Thonotosassa, FL (US); Gary A. Luzio, Winter Haven, FL (US); Thomas G. McCollum, Vero Beach, FL (US); Prasanna Vasu, Jonesboro, AR (US); Alberto Nunez, Dresher, PA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 141 days.

(21) Appl. No.: 11/986,187

(22) Filed: Nov. 20, 2007

(65) Prior Publication Data

US 2009/0130722 A1 May 21, 2009

(51) Int. Cl.
*C12N 9/00* (2006.01)
*C12N 9/16* (2006.01)
*C12N 9/18* (2006.01)
*C12N 1/20* (2006.01)
*C12N 15/00* (2006.01)
*C07H 21/04* (2006.01)

(52) U.S. Cl. .................. 435/197; 435/183; 435/196; 435/252.3; 435/320.1; 536/23.2

(58) Field of Classification Search ............ None
See application file for complete search history.

(56) References Cited

U.S. PATENT DOCUMENTS

| 6,069,000 | A | 5/2000 | Andersen et al. |
| 6,268,195 | B1 | 7/2001 | Christensen et al. |
| 6,627,429 | B1 | 9/2003 | Christensen et al. |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Cameron, Randall G. et al., "Separation and Characterization of a Salt-Dependent Pectin Methylesterase from *Citrus sinensis* Var. Valencia Fruit Tissue," *Journal of Agricultural and Food Chemistry*, 2003, vol. 51, pp. 2070-2075.
Cameron, Randall G. et al., "Multiple Forms of Pectinmethylesterase from Citrus Peel and Their Effects on Juice Cloud Stability," *Journal of Food Science*, 1998, vol. 63, No. 2, pp. 253-256.
Christensen, Tove M.I.E. et al., "Pectin methyl esterase from orange fruit: Characterization and Localization by in-situ hybridization and immunohidyochemistry,"*Planta*, 1998, vol. 206, pp. 493-503.
Corredig, Milena et al., "Particle Size Distribution of Orange Juice Cloud after Addition of Sensitized Pectin," *Journal of Agricultural and Food Chemistry*, 2001, vol. 49, pp. 2523-2526.
Arias, Covadonga R. et. al., "A Pectinmethylesterase Gene Associated with a Heat-Stable Extract form Citrus," *Journal of Agricultural and Food Chemistry*, 2002, vol. 50, pp. 3465-3472.

Hotchkiss Jr., Arland T. et al., "Enzymatic Modification of Pectin to Increase its Calcium Sensitivity while preserving its Molecular Weight," *Journal of Agricultural and Food Chemistry*, 2002, vol. 50, pp. 2931-2937.
Joye, D.D. et al., "Process for selective extraction of pectins from plant material by Differential pH," *Carbohydrate Ploymers*, 2000, vol. 43, pp. 337-342.
Markovic, Oskar et al., "Pectin methylesterases: sequence-structual features and phylogenetic relationships," *Science Direct*, 2004, vol. 339, pp. 2281-2295.
Micheli, Fabienne, "Pectin methylesterases: cell wall enzymes with important roles in Plant Physiology," *TRENDS in Plant Science*, Sep. 2001, vol. 6, No. 9, pp. 414-419.
Narin, Joseph C. et al., "Genetics and expression of two pectinesterase genes in Valencia Orange," *Physiologia Plantarum*, 1998, vol. 102, pp. 226-235.
Pelloux, Jerome et al., "New insights into pectin methylesterase structure and function," *Trends in Plant Science*, vol. 12, No. 6, pp. 267-277.
Savary, Brett J. et al., "Characterization of a Salt-Independent Pectin Methylesterase Purified from Valencia Orange Peel," *Journal of Agricultural and Food Chemistry*, 2002, vol. 50, 3553-3558.
Wicker, L. et al., "Modification of Pectin by pectinmethylesterase and the role in Stability of Juice Beverages," *Food Hydrocolloids*, 2003, vol. 17, pp. 809-814.
Willats, William G.T. et al., "Modulation of the Degree and Pattern of Methyl-estrification of Pectic Homogalacturonan in Plant Cell Walls," *The Journal of Biological Chemistry*, Jun. 1, 2001, vol. 276, No. 22, pp. 19404-19413.

* cited by examiner

*Primary Examiner*—Christian L Fronda
(74) *Attorney, Agent, or Firm*—John D. Fado; Evelyn M. Rabin

(57) ABSTRACT

Enzymes accumulated in plant cell walls serve diverse physiological functions including metabolism, polysaccharide structure modification, and molecular communication in interactions with other organisms. Pectin methylesterases are economically important enzymes for their impact on quality and processing properties of fruit and vegetable food products. We have now purified TT-PME to homogeneity from sweet orange finisher pulp and determined the complete corresponding nucleic acid sequence. Purified TT-PME was observed by SDS-PAGE as two doublet bands with molecular masses of approximately 46,000 Da and 56,000 Da. Direct Edman sequencing from these proteins showed a common N-terminal peptide. De novo sequencing of eight TT-PME tryptic peptides determined by MALDI-TOF/TOF mass spectrometry provided additional internal sequences. TT-PME did not correspond to any previously reported *Citrus* spp. PME sequence. Our results show *Citrus* TT-PME is a distinctive new isoform with phylogenetic relationship closer to PME isoforms in other species rather than to previously described *Citrus* PME genes.

9 Claims, 12 Drawing Sheets

A

| Mass | Peptide Sequence | Notes | SEQ ID NO: |
|---|---|---|---|
| 794.46 | HQAVALR | | 17 |
| 872.49 | (N.D.) | NIITAQGR* | 18 |
| 878.45 | VTWPGYR | | 19 |
| 1020.56 | TYLGRPWK | | 20 |
| 1074.51 | (N.D.) | SGSDLSAFYK* | 21 |
| 1159.59 | (N.D) | GITVENSAGPSK* | 22 |
| 1167.59 | (N.D.) | SVVDGWTTFR* | 23 |
| 1268.64 | TMLMFVGDGIGK | Double $M_{Ox}$ 1300.63 | 4 |
| 1320.75 | SATVAVVGTGFIAK | | 5 |
| 1341.63 | KAYFENVEVSR | AGAYFENVEVDK* | 15; 16 |
| 1652.85 | VAAASDLLPYQTEFK | (L or I) | 24 |
| 1887.90 | CSFVGYQDTLYVHSLR | | 25 |

B

| | | | |
|---|---|---|---|
| TT-PME | | | |
| Flavedo | 35 | HDLQTLFSGAMTNQYTCLDGFAYSDGNVRDVIKSSLYNISRHVSNSLVMLKKIPGDNM | 92 |
| Ovary | 7 | GAMTNQYTCLDGFAYSDGNVRDVIKSSLYNISRHVSNSLVMLKKIPGDNM | 56 |
| Mixed | 82 | HDLQTLFSGAMTNQYTCLDGFAYSDGNVRDVIKSSLYNISRHVSNSLVMLKKIPGDNM | 139 |

TT-PME
              LQKSVXLTKFDLIVAKD

| | | | |
|---|---|---|---|
| Flavedo | 93 | SSKYEVFPEYGRIKRGFPTWLSLNDRKLLQKSVNLTKFDLIVAKDGSGNFTTITEAVE | 140 |
| Ovary | 57 | SSKYEVFPEYGRIKRGFPTWLSLNDRKLLQKSVNLTKFDLIVAKDGSGNFTTITEAVE | 113 |
| Mixed | 140 | SSKYEVFPEYGRIKRGFPTWLSLNDRKLLQKSVNLTKFDLIVAKDGSGNFTTITEAVE | 197 |

TT-PME
                     KAYFENVEVSR   TMLMFVGDGIGK

| | | | |
|---|---|---|---|
| Flavedo | 141 | AAPNKSNTRFVIYIKAGAYFENVEVDKKKTMLMFVGDGIGKTVVKANRSVVDGWTTFR | 198 |
| Ovary | 114 | AAPNKSNTRFVIYIKAGAYFENVEVDKKKTMLMFVGDGIGKTVVKANRSVVDGWTTFR | 171 |
| Mixed | 198 | AAPNKSNTRFVIYIKAGAYFENVEVDKKKTMLMFVGDGIGKTVVKANRSVVDGWTTFR | 255 |

TT-PME     SATVAVVGTGFIAK               HQAVALR                            CSFVGYQDTLYVHSLR

| | | | | |
|---|---|---|---|---|
| Flavedo | 199 | SATVAVVGTGFIAKGITVENSAGPSKHQAVALRSGSDLSAFYKCSFVGYQDTLYVHSL | 229 | SEQ ID:26 |
| Ovary | 172 | SATVAVVGTGFIAKGITVENSAGPSKHQAVALRSGSDLSAF | 229 | SEQ ID:27 |
| Mixed | 256 | SATVAVVGTGFIAKGITVENSAGPSKHQAVALRSGSDLSAF | 306 | SEQ ID:28 |

FIG. 10

```
5'-                                                                                                              -3'
atgtatagtcccactcccagtcccaggcgaagaaccagactcttacttgctctcttacccagttcagctattttcttgctactatttgtactatcagct
 M  Y  S  P  T  P  S  P  R  R  R  T  R  L  L  L  A  L  L  P  S  S  A  I  F  L  L  L  F  V  L  S  A gtaagtgtaaccaccctcaaaaagaaccccaaaacaacagatgccccacacttgcgagtccataaacatttccaggttgctcattccgcatgcgaaggc
 V  S  V  T  T  L  K  K  N  P  K  T  T  D  A  P  H  L  R  V  H  K  H  F  Q  V  A  H  S  A [C] E  G
acactctatcctgaactctgcgtttcgactctgctttcagtcccagatctcgcttcaaaaagagtccctgaactcatctccgtaaccataaaccgcaca
 T  L  Y  P  E  L [C] V  S  T  L  L  S  V  P  D  L  A  S  K  R  V  P  E  L  I  S  V  T  I  N  R  T
ttgtccgagctgagagcctcctcctcaaactgctccagcattggacagagttacccaaattttaaccccttgaaaagagagcaatcaatgactgtctc
 L  S  E  L  R  A  S  S  S  N [C] S  S  I  G  Q  S  Y  P  N  F  N  T  L  E  K  R  A  I  N  D [C] L
gagctgtttcatgacaccattgttgagctcaaatcagctctcaatgatctctccccaagaaatcgccctccaagcattaccatgatttgcaaactttg
 E  L  F  H  D  T  I  V  E  L  K  S  A  L  N  D  L  S  P  K  K  S  P  S  K  H  Y  H  D  L  Q  T  L
tttagcggtgcaatgacaaaccagtacacgtgtcttgatgggttcgcttacagtgacggaaacgtgagggaagttattaagagcagcttgtacaacatt
 F  S  G  A  M  T  N  Q  Y  T [C] L  D  G  F  A  Y  S  D  G  N  V  R  E  V  I  K  S  S  L  Y  N  I
tccaggcacgtgagcaactctttggtcatgctcaagaaaatccccggtgataacatgtcttccaagtacgaggttttcctgagtatgggcgtattaag
 S  R  H  V  S  N  S  L  V  M  L  K  K  I  P  G  D  N  M  S  S  K  Y  E  V  F  P  E  Y  G  R  I  K
agaggattcccaacttggttgtctttaaatgatcgcaaattg-3'
 R  G [F  P  T  W  L  S  L  N  D  R  K  L]
                                            ↓  ↓
                                    5'-ttacagaagtccgttaatttgaccaaatttgatctgatagtggctaaagatggctct
                                      [L  Q  K  S  V  N  L  T  K  F  D  L  I  V  A  K  D] G  S
gggaatttcactaccattactgaagcagtggaagcagctccaaacaaatccaatactcggttgtgatttacataaaagctggggcttattttgagaac
 G  N  F  T  T  I  T  E  A  V  E  A  A  P  N  K  S  N  T  R  F  V  I  Y  I  K [A  G  A  Y  F  E] N
gtggaggtggataaaagaagacaatgttgatgttcgtaggagatgggatcggcaaaacattagtgaaggccaatagaagcgtcgttgatggatggact
 V  E  V  D  K  K  K  T  M  L  M  F  V  G  D  I  G  K  T  L  V  K  A  N  R  S  V  V  D  G  W  T
actttccggtcagccactgtagctgtggtggggaccgggtttatcgccaaaggcattacagttgagaactcagctggtccaagcaaacaccaagcagta
 T  F  R  S  A  T  V  A  V  V  G  T  P  F  I  A  K  G  I  T  V  E  N  S  A  G  P  S  K [H  Q  A  V→
gccttaaggagtggctcagatctctcagctttctacaaatgcagcttcgttgggtaccaagacactctatatgttcattccctcagacaattttatcgt
 A  L  R] S  G  S  D  L  S  A  F  Y  K  C  S  F  V  G [Y  Q  D  T  L  Y  V] H  S  L  R  Q  F  Y  R
gaatgcgacgtatatggcacagttgatttcatctttggcaatgcagctgtgttccaaatctgcaacttatatgcccgtaagccaaatgcaaaccaa
 E  C  D  V  Y  G  T  V [D* F  I  F  G] N  A  A  V  V  F  Q  I  C  N  L  P  N  Q  N  T  G  I  S  I
aaaaatattatcactgcacaggggagagaagaccctaatcaaaatacaggatatcatcttgaattgcaaagttgctgctgcttcggacttgattcca
 Y  A  R  K  P  N  A  N  Q  K  N  I  I  T  A  Q  G  R  E  D  L  N  C  K  V  A  A  A  S  D  L  I  P
tatcaaacagagtttaaaacataccttggtcgtccttggaaagaatattcgaggacggttttttatgctatcttatttgggcgatttgatagcgccggct
 Y  Q  T  E  F  K  T  Y [L  G  R* P  W* K] E  Y  S  R  T  V  F  M  L  S  Y  L  G  D  L  I  A  P  A
ggatggttagaatggaatggtacatttgcattgagtacactcttttacggggagtacaagaacagggggccctggttctaacacgagtgccagagtgacg
 G  W  L  E  W  N  G  T  F  A  L  S  T  L  F  Y  G  E  Y  K  N  R  G  P  G  S  N  T  S  A  R  V  T
tggcctggttacagggtgatcaataactcggctgtggcagctcaatttacggccgggccattcttgcaaggaagtgaatggctaaattctactggcatt
 W  P  G  Y  R  V  I  N  N  S  A  V  A  A  Q  F  T  A  G  P  F  L  Q  G  S  E  W  L  N  S  T  G  I
cctttctatctcaatttgactccttga-3'    SEQ ID NO: 1 DNA
 P  F  Y  L  N  L  T  P  -          SEQ ID NO: 2 Protein
```

FIG. 11

| Mass | Position | Peptide Sequence | SEQ ID NO: |
|---|---|---|---|
| 661.388 | 4-9 | SVNLTK | 29 |
| 805.482 | 10-16 | FDLIVAK | 30 |
| 1921.914 | 17-35 | DGSGNFTTITEAVEAAPNK | 31 |
| 782.481 | 40-45 | FVIYIK | 32 |
| 1341.632 | 46-57 | AGAYFENVEVDK | 16 |
| 1268.638 | 60-71 | TMLMFVGDGIGK | 4 |
| 1167.579 | 79-88 | SVVDGWTTFR | 23 |
| 1320.75 | 89-102 | SATVAVVGTGFIAK | 5 |
| 1159.595 | 103-114 | GITVENSAGPSK | 22 |
| 794.463 | 115-121 | HQAVALR | 17 |
| 1074.510 | 122-131 | SGSDLSAFYK | 21 |
| 1887.906 | 132-147 | CSFVGYQDTLYVHSLR | 15 |
| 613.309 | 148-151 | QFYR | 33 |
| 3027.438 | 152-178 | ECDVYGTVDFIFGNAAVVFQICNLYAR | 34 |
| 799.442 | 179-185 | KPNANQK | 35 |
| 872.495 | 186-193 | NIITAQGR | 18 |
| 1645.785 | 194-208 | EDPNQNTGISILNCK | 36 |
| 1652.853 | 209-223 | VAAASDLIPYQTEFK | 24 |
| 1020.563 | 224-231 | TYLGRPWK | 20 |
| 554.257 | 232-235 | EYSR | 37 |
| 3973.976 | 236-270 | TVFMLSYLGDLIAPAGWLEWNGTFALSTLFYGEYK | 38 |
| 846.406 | 273-281 | GPGSNTSAR | 39 |
| 878.452 | 282-288 | VTWPGYR | 19 |
| 3837.949 | 289-324 | VINNSAVAAQFTAGPFLQGSEWLNSTGIPFYLNLTP | 40 |

FIG. 12

THERMALLY-TOLERANT PECTIN METHYLESTERASE

BACKGROUND OF THE INVENTION

1. Field of the Invention

This invention relates to a polypeptide having thermally-tolerant pectin methylesterase activity, a gene encoding the polypeptide, a method of producing the polypeptide, a process for isolating the polypeptide, compositions comprising the polypeptide, and methods of using the polypeptide and compositions.

2. Description of the Relevant Art

Processed *citrus* juice from Florida (predominantly from oranges) is currently valued as an approximately $2.86 billion industry (Hodges et al. 2006. *EDIS Document FE*633, Institute of Food and Agricultural Sciences, University of Florida, Gainesville, Fla.). Product quality is largely defined by juice cloud properties such as turbidity, flavor, aroma, and color (Baker and Cameron. 1999. *Food Technol*. 53: 64-69). Cloud loss is a defect largely attributable to the enzyme pectin methylesterase (PME) (Rouse, A. H. 1949. *Proc. Florida State Hort. Soc.* 62: 170-173). PME acts on pectin associated with juice cloud, leading to aggregation through calcium cross-linking and subsequent cloud separation (Baker and Cameron, supra; Croak and Corredig. 2006. *Food Hydrocolloids* 20: 961-965). Multiple forms of PME are present in juice, but only certain PME forms are responsible for juice cloud separation (Versteeg et al. 1980. *J. Food Sci.* 45: 969-971, 998; MacDonald et al. 1993. *J. Sci. Food Agric.* 62: 163-168; Cameron et al. 1998. *J. Food Sci.* 63: 253-256). Variance in action on pectin may represent differences in mechanism of action by PME isoforms.

*Citrus* juice peel contains 10-15% pectin on a fresh weight basis (Grohmann and Baldwin. 1992. *Biotechnol. Lett.* 14: 1169-1174; Grohmann et al. 1995. *Biores. Technol.* 54: 129-141). Pectin, a complex polysaccharide, is composed of at least five different sugar moieties, but 80-90% of its dry weight is galacturonic acid. The vast majority of the galacturonic acid is found in homogalacturonan regions of pectin, regions of unbranched polymers of galacturonic acid in which a variable proportion of the galacturonic acid residues may contain a methyl ester at their C6 position. The functional properties of pectin are thought to be dependent on the fraction of these galacturonic acid residues that are methylated and their distribution along the homogalacturonan stretches (Taylor, A. J. 1982. *Carbohydrate Polymers* 2: 9-17; Willats et al. 2001. *J. Biol. Chem.* 276: 19494-19413). Two patterns of methyl ester distribution are generally recognized, either random or ordered, i.e., blockwise (Willats et al., supra). Analyzing these patterns of demethylation is key to understanding their relationship to function.

*Citrus* juice cloud stability and the functional properties of commercial *citrus* pectin are related to the pectin molecular weight (Hotchkiss et al. 2002. *J. Agric. Food Chem.* 50: 2931-2937), degree of methylesterification (Hills et al., 1949. *Food Technol.* 3: 90-94), and intramolecular distribution of the methyl ester blocks within the population of pectin molecules (Joye and Luzio. 2000. *Carbohydr. Polym.* 43: 337-342; Willats et al., supra; Baker, R. A. 1979. *J. Agric. Food Chem.* 27:1387-1389; Wicker et al. 2003. *Food Hydrocolloids* 17: 809-814). Sequential cleavage of the C6 methyl esters of galacturonic acid residues in pectin produces a distribution of "blocks" of free acid groups. When of sufficient size, such blocks on adjacent pectin molecules can be cooperatively cross-linked by divalent cations, leading to precipitation of the pectins. In the presence of juice cloud and adequate serum calcium ions, this precipitation entrains and removes the cloud particulates resulting in an unattractive, largely flavorless clear serum, deficient in sensory properties (Cameron et al. 1998, supra). Although a minimal block size of nine unesterified galacturonic acid residues has been hypothesized to be necessary for calcium cross-linking, a larger de-esterified block might be necessary for gel formation (Liners et al. 1992. *Plant Physiol.* 99: 1099-1104; Corredig et al. 2001. *J. Agric. Food Chem.* 49: 2523-2526). Gelation in juice concentrates may vary from slight curdiness to firm gels, which are unsightly and can hinder reconstitution (Cameron et al. 1998, supra). Approximately 25-20% of cloud-associated pectin has been reported to be calcium pectate (Klavons et al. 1994. *J. Food Sci.* 59: 399-401). High-methoxy pectins in which de-esterified blocks allow them to gel in the presence of calcium without the addition of sucrose are termed calcium-sensitive pectins (Hills et al., supra; Joye and Luzio, supra). Two thermally labile pectin methylesterases (TL-PMEs) from *citrus* fruit pulp tissue have been demonstrated to be blockwise demethylating enzymes, introducing calcium sensitivity into a non-calcium-sensitive pectin (NCSP) with very limited reduction (6.0%-6.5%) in their degree of methylesterification (Savary et al. 2001. *J. Agric. Food Chem.* 50: 3553-3558; Cameron et al. 2001. *J. Agric. Food Chem.* 51: 2070-2075).

Pectin methylesterases (PMEs) are cell wall polysaccharide-modifying enzymes (EC 3.1.1.11) that act to hydrolyze the C6-carboxyl methyl esters decorating homo-galacturonan regions of pectin described above (Bordenave, M. 1996. In: *Plant Cell Wall Analysis*, Linskens and Jackson, eds., Springer-Verlag, New York, pp. 165-180; Micheli, F. 2001. *Trends Plant Sci.* 6: 414-419; Markovč and Janeček. 2004. *Carbohyd. Res.* 339: 2281-2295). Thus, control of these enzyme activities in juice processing from fruit species such as *Citrus* is critical for quality and stability of fruit juices (Klavons et al., supra; Goodner et al. 1998. *J. Agric. Food. Chem.* 46: 1997-2000; Baker and Cameron, supra). PME action to de-esterify pectin in juice cloud colloidal structures results in calcium-mediated agglomeration and subsequent irreversible cloud separation, thus yielding degraded juice. *Citrus* species produce multiple forms of PMEs in fruit tissues (Versteeg et al. 1980, supra; Seymour et al. 1991a. *J. Agric. Food. Chem.* 39: 1080-1085; Seymour et al. 1991b. *J. Agric. Food. Chem.* 39:1075-1079; MacDonald et al., supra; Cameron et al. 1998, supra.

PMEs are present as a large multi-gene family in plants (Micheli, supra; Markovič and Janeček, supra; Pelloux et al. 2007. *Trends Plant. Sci.*, 12: 267-277). They appear to represent the largest cell wall-related gene families in both *Arabidopsis* and *Oryza* (Yokoyama and Nishitani. 2004. *Plant Cell Physiol.* 45: 111.1-1121). As many as seven unique nucleic acid sequences have been obtained from orange and reported to public sequence databases, and their sequence similarities indicate they represent variants of the two major TL-PMEs (Nairn et al. 1998. *Physiol. Plant* 102: 226-235; Christensen et al. 1998. *Planta* 206:493-503; Arias and Burns. 2002. *J. Agric. Food. Chem.* 50: 3465-3472). Other partial PME-like sequences are present in *Citrus sinensis* EST sequence libraries (Bausher et al. 2003. *Plant Sci.* 165: 415-422; Savary et al. 2003. In: *Advances in Pectin and Pectinase Research*, Voragen et al., eds., Kluwer Academic Publishers, Netherlands, pp. 345-361). Some PMEs and their genes have been isolated from plants, bacteria and fungi and have been patented for use in modifying food hydrocolloids (Christensen et al. 2001 U.S. Pat. No. 6,268,195 Christensen et al. 2003 U.S. Pat. No. 6,627,429; Andersen et al. 2000. U.S. Pat. No. 6,069,000).

At the protein level, only the two major thermally-labile orange PMEs (TL-PME) have been purified to homogeneity to provide amino acid sequence information in conjunction with biochemical properties. The two PMEs are represented by what have been described as salt-independent peak 2 PME, PME2 (Savary et al. 2002. *J. Agric. Food. Chem.* 50: 3553-3358) and salt-dependent peak 4 PME, PME4 (Cameron et al. 2003. *J. Agric. Food Chem.* 51: 2070-2075). In Valencia orange, the most abundant PME form present in pulp tissue, the thermolabile salt-independent PME2, readily destabilizes juice at room temperature (Cameron et al. 1998, supra; Savary et al. 2002, supra).

However, it is the thermally tolerant PME (TT-PME) that it is most significant in destabilizing juice cloud under cold storage at 4° C. (Versteeg et al., 1980, supra; Cameron et al.,1998, supra). TT-PMEs have been found in lemon juice, grapefruit pulp, *citrus* tissue culture cells, commercial fresh frozen Valencia orange juice, and other sweet orange varieties (MacDonald et al., supra; Seymour et al., supra; Cameron and Grohmann. 1995. *J. Food Sci.* 60: 821-825; Cameron et al. 1994. *J. Agric. Food Chem.* 42: 903-908; Cameron et al. 1996. *J. Food Sci.* 62: 242-245; Snir et al. 1996. *J. Food Sci.* 61: 379-382). TT-PME is found in less abundance than the TL-PMEs; however, its considerable tolerance to heat inactivation necessitates that it be strictly controlled during processing in order to stabilize juice cloud (Cameron and Grohmann. 1996. *J. Agric. Food. Chem.* 44: 458-462; Baker and Cameron, supra). Pasteurization of juice at approximately 20° C. above that temperature considered necessary to control microbial growth is required to effectively inactivate TT-PME (Eagerman and Rouse. 1976. *J. Food Sci.* 41: 1396-1397; Chen et al., 1998. *J. Agric. Food Chem.* 46: 1777-1782).

There is a problem of continuing uncertainty in the food biochemistry literature regarding PME behavior in juice and in vitro systems due to inadequate or ambiguous identification of the protein isoforms present in the preparations that have been studied. This is a critical issue, since various PME isoforms are known to be present in the same preparation and do not have identical biochemical properties and their action on pectin and ability to de-stabilize juice cloud vary (Versteeg et al., 1978. *Lebensm-Wiss. Technol.* 11: 267-274; MacDonald et al., 1996; Cameron et al., 1998, supra; Catoire et al. 1998. *J. Biol. Chem.* 273: 3310-3315; Corredig and Wicker. 2002. *J. Food Sci.* 67: 1668-1671).

To address isoform identification, we applied matrix-assisted laser desorption ionization mass spectrometry (MALDI-TOF MS) and associated proteomics tools as a direct means to readily identify the two major orange TL-PMEs by matching tryptic peptides to their corresponding translated nucleotide sequences (Savary et al., 2007). Coupling this analytical technology with homogeneous protein preparations resulted in unequivocal structural evidence that the salt-independent TL-PME2 is encoded by the gene deduced from the sequence of the ~36 kDa protein that Arias and Burns (supra) identified as associated with thermostable PME activity.

TT-PME (peak 3 PME, Cameron et al., 1998, supra) has been reported to be of higher molecular weight than the TL-PME isoforms, with sizes estimated as 40,000-43,000 to 51,000-53,000 (Versteeg et al. 1980, supra; Seymour et al., supra; Cameron and Grohman, 1996, supra; Cameron et al. 2005. *J. Agric. Food Chem.* 53:2255-2260). We had previously correlated TT-PME activity to a 41,000 glycoprotein by denaturing PAGE (Cameron et al, 1995; Cameron et al., 2005, supra). However, the N-terminal peptide sequences and MALDI-TOF MS spectra obtained from this 41,000 glycoprotein suggested identity to polygalacturonase inhibitor proteins (PGIPs). PGIPs are monomeric cell wall-associated proteins in *citrus* fruit regarded as defensive proteins that act to modify action of fungal pathogen polygalacturonases (D'hallewin et al. 2004. *Physiol. Plant* 120:395-404; Kemp et al. 2004. *Plant-Microbe Interact.* 17: 888-894; Federici et al. 2006. *Trends Plant Sci.* 11:65-70). A dual-functional protein, containing both PME and PGIP activities, would be remarkable but not unprecedented (Sharma et al. 2004. *Plant Physiol.* 134: 171-181; Roopashree et al. 2006. *Biochem. J.* 395: 629-639). If both activities are indeed present in a single protein, possession of a methylesterase activity would suggest a mechanism for how certain PGIPs may activate some fungal polygalacturonases (Kemp et al., supra). However, we were unable to either confirm dual activity for orange PGIP or demonstrate co-purification of a more abundant second protein—a PGIP with nearly identical physicochemical properties—with the protein responsible for TT-PME activity; our efforts to confirm identification were hampered by insufficient quantities of protein (Cameron et al., 2005, supra).

TT-PME activity is present as a small portion of total extractable PME activity in *Citrus* fruit (Seymour et al., supra; Snir et al, supra; MacDonald et al. 1994. *J. Sc. Food Agric.* 64: 129-134; Cameron et al., 1998, supra). Purification of TT-PME is further hampered by the presence of soluble pectinates co-extracted during PME isolation (Versteeg et al. 1980, supra; Snir et al., 1995; MacDonald et al., 1996; Cameron et al., 1998, supra). This has led to complex purification schemes, insoluble precipitates, and low yields. Given the difficulties presented by the low amounts of TT-PME activity measured and the presence of pectinates, previous experimental preparations could not conclusively associate TT-PME activity in the juice cloud with a protein having a definitive size, structure, sequence, and identifying biochemical characteristics.

Thus, TT-PME is a key fruit cell wall enzyme. There exists a need to improve the strategy for purifying orange TT-PME, and thereby enabling the isolation of a electrophoretically pure protein and establishing its unambiguous identification as a TT-PME with regard to its size, structure, sequence, and characteristic activity. We have developed a simplified purification method that provides greatly improved yield and purity of a TT-PME. The enzyme thus prepared was used to establish the identity of a novel TT-PME by biochemical assays, MALDI-TOF MS sequencing, and determination of its complete nucleotide sequence.

SUMMARY OF THE INVENTION

We have identified a novel thermally-tolerant pectin methylesterase, TT-PME.

In accordance with this discovery, it is an object of the invention to provide an isolated TT-PME and compositions comprising TT-PME.

It is another object of the invention to provide an isolated, recombinant TT-PME and compositions comprising TT-PME.

It is a further object of the invention to provide an isolated nucleic acid molecule which encodes the TT-PME.

It is an additional object of the invention to provide a method of purifying TT-PME protein.

It is still another object of the invention to provide a method of using TT-PME to treat pectin-containing plant material to reduce the viscosity or to improve processing or appearance of plant material.

Other objects and advantages of this invention will become readily apparent from the ensuing description.

BRIEF DESCRIPTION OF THE DRAWINGS

FIG. 5A shows the total protein extracted from washed finisher orange pulp before (lane 1; ~20 μg loaded) and after (lane 2; ~10 μg loaded) heat-treatment for 30 min at 70° C. FIG. 5B depicts proteins purified following separation of pectinates and PMEIP-affinity chromatography. Before (lane 1) and after (lane 2) reheating to preparation to 70° C. Replicate gels were run to recover protein bands a-d (indicated by arrows at right margin of gels) for direct N-terminal sequencing and/or MALDI-TOF MS peptide mass fingerprinting. Molecular weight markers (Invitrogen) used are indicated at left margin of gels: SeeBlue-Plus 2 (A) and Mark-12 (B).

FIG. 10 shows the amino acid sequence alignment from three translated *Citrus* EST cDNAs with TT-PME peptides. TT-PME: peptides determined directly from purified protein. Flavedo: peptides deduced from *C. sinensis* developing fruit flavedo at 80 DAFB cDNA clone (CK936641); 5'3' Frame 2 translation. Ovary: peptides deduced from *C. sinensis* ruby orange ovary at anthesis cDNA clone (CF833608); 5'3' Frame 1 translation. Mixed: peptides deduced from *C. clementina* adult, mixed tissue cDNA (DY285162); 5'3' Frame 3 translation. Peptide sequences aligned in boxes readily matched to the three translated EST sequences by BLAST.

FIG. 11 shows the nucleic acid (SEQ ID NO:1) and translated protein sequence (SEQ ID NO:2) for TT-PME separated into signal peptide (A), propeptide (B), and mature protein (C). The cleavage site between the signal peptide (33 amino acids) and the propeptide (212 amino acids) was predicted by using SignalP tool. The N-terminal sequence (17 amino acid peptide in brackets) of mature protein was determined directly from protein. Eight peptides determined by MS/MS de novo sequencing from the TT-PME tryptic digest are underlined. Thirteen N-X-S/T N-glycosylation sequons are indicated in bold. Those likely glycosylated are in italics (NetNGly tool). Five cysteine residues and the peptide sequence conserved in the propeptide of Clade 1 of plant PMEs (Markovič and Janaček, 2004) are marked in boxes. Five additional sequence elements conserved in plant PMEs are also indicated in boxes in mature protein (Markovič and Janaček, 2004). Residues identified in the active site of the enzyme are indicated by an asterisk (*) (Markovič and Janaček, 2004).

FIG. 12 depicts the full tryptic peptide set generated from the TT-PME sequence. The set excludes peptides with mass <600 Da and masses are not corrected for methionine oxidation or asparagine glycosylation.

DETAILED DESCRIPTION OF THE INVENTION

Figure 1:
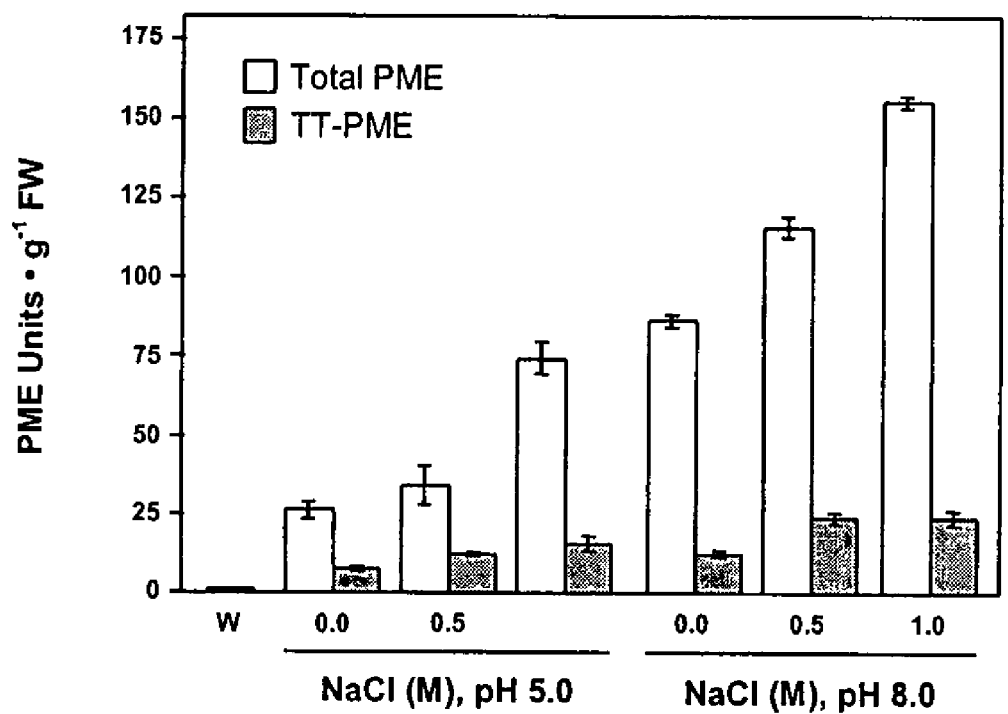
FIG. 1 depicts PME extraction from orange finisher pulp under different pH and salt conditions. Finisher pulp was washed with salt-free water (W, wash solutions measured pH 3.4) prior to extraction with acetate (100 mM, pH 5.0) or Tris (100 mM, pH 8.0) buffers containing either 0, 0.5, or 1.0 M sodium chloride. Clarified extracts were assayed for total PME activity, then heated 40 min at 70° C. to determine fraction of TT-PME activity.

The invention provides a novel pectin-modifying protein; namely, a novel thermally-tolerant pectin methylesterase (TT-PME).

Pectin methylesterases (PMEs) have been isolated and studied, but as discussed above, PME activities measured under standardized assay conditions are not easily correlated to activities related to their effects during destabilization of juice. Multiple forms from this large gene family, and additional variants due to posttranslational modifications, can have variable effects that are difficult to measure and correlate with particular biological or functional properties.

We have isolated the novel TT-PME as an electrophoretically pure enzyme from sweet orange fruit (*Citrus sinensis* var. Valencia), i.e., the TT-PME is free of other PME isoforms or pectin-active enzyme activities. We have established its identity as a novel TT-PME by biochemical assays, MALDI-TOF MS sequencing, and determination of its complete nucleotide sequence.

TT-PME was isolated using an extraction process combining ultrafiltration, heat treatment, differential adsorption of pectinates, and selective affinity-binding to immobilized PME-IP (See Examples 1 and 3). During the preparative extraction, the extract was filtered and then concentrated by tangential-flow ultrafiltration. The filtered and clarified extract was heat-treated and then subsequently treated with DEAE-Sepharose to remove co-extracted soluble pectinates having a relatively high charge density. The DEAE-treated extract was analyzed for galacturonic acid content and clearance of contaminating pectinates was confirmed.

PME activity was isolated from the pectinate-free DEAE-treated extract using a PME-inhibitor protein (IP) affinity chromatography column. The binding of PME in the extract to the inhibitor protein (IP) immobilized on the column is due to structural recognition; the two proteins form a stoichiometric 1:1 complex in which the inhibitor covers the shallow cleft of the enzyme where the putative active site is located (Di Matteo et al. 2005. *The Plant Cell* 17:849-858). The TT-PME eluted from the PME-IP column represents a 163-fold purification as compared to the starting material. This result represents a better than a 10-fold improvement in yield over prior reports for any *Citrus* PME purification.

Analysis of the purified TT-PME by SDS-PAGE identified two pairs of doublet bands with molecular masses estimated at 55.3 kDa and 56.5 kDa and 46.0 kDa and 47.2 kDa. Two bands were further resolved in the 56 kDa band in separate experiments by differential binding to Con-A Sepharose and by running a 10% PAGE gel. Thus, the TT-PME isolated and purified by the purification strategy of the invention and analyzed by SDS-PAGE represents a novel TT-PME based on its molecular mass. In a previous report describing TT-PME activity (Cameron et al., 2005, supra), we associated TT-PME activity with a diffuse 40.8 kDa band. In this study, a ~41 kDa protein was shown to be eliminated by heat treatment and PME-IP affinity chromatography; it was found only in unbound flow-through fraction. MALDI-TOF MS analysis confirmed its identity as PGIP protein (Prasanna et al., manuscript in preparation). Thus, the previously identified ~41 kDa protein is not a TT-PME.

Of further note as a point of clarifying the record related to PMEs identified as TT-PME, a protein evident in the crude finisher pulp extract that we estimate as 34 kDa was observed bound to the PME-IP affinity column. Its identity was confirmed as TL-PME2 by MALDI-TOF MS (Savary et al., submitted). Thus, although the 34 kDa TL-PME2 protein was completely inactivated by heat, i.e., it is thermally labile, a portion of it remained sufficiently soluble following heat treatment, and it was still capable of binding to the inhibitor protein. Its solubility was presumably stabilized by the presence of co-extracted pectinates. Heat treatment of highly purified PME2 (Savary et al. 2003, supra) does not result in residual soluble protein (results not shown). Thus, these results can explain how the preparation by Arias and Burns (supra) inadvertently resulted in the salt-independent TL-PME2 being used to generate a synthetic gene for cloning and sequencing a "thermally-stable" PME based on their assumption that it represented the "thermally-stable" PME activity, since it had remained present in their heat-treated preparation.

The four TT-PME bands resolved by SDS-PAGE were each trypsin digested and evaluated by MALDI-TOF MS. Consistent with the four having a common N-terminal peptide, a common peptide mass fingerprint was observed for them and twelve significant peptide ions were consistently observed (See FIGS. 8 and 9). Automated MASCOT evaluation of the spectra provided protein scores suggesting a closer relationship to rice and *Arabidopsis* PME sequences than to known *Citrus* PMEs; unequivocally, TT-PME did not match with any *Citrus* PME sequence in the non-redundant database.

A synthetic gene was generated on the basis of the amino acid sequence of peptides of the isolated TT-PME bands. Direct Edman sequencing revealed a common N-terminal peptide. De novo sequencing of eight TT-PME tryptic peptides determined by MALDI-TOF/TOF mass spectrometry provided additional internal sequences. to generate the full-length cDNA sequence for TT-PME.

The TT-PME tryptic peptides were overlaid with alignment of the three translated amino acid sequences from *Citrus* EST cDNAs that were initially identified with the N-terminal peptide. Using at least two overlapping peptide or translated nucleotide sequences to establish likely sequence, a common 232 amino acid polypeptide was obtained that overlapped part of the pro-peptide and mature protein sequences (See FIG. 10). The common 591 nucleotide base sequence from all three *Citrus* EST sequences was used for selecting primers (Table 3) for RT-PCR experiments and for subsequent RACE-PCR experiments to generate the full-length cDNA sequence for TT-PME.

In conclusion, we have demonstrated that TT-PME can be readily recovered in high yield from finisher pulp under conditions that are directly amenable to large-scale preparation. Ammonium sulfate precipitation and dialysis steps are eliminated by separating problematic pectinates with high capacity anion-exchangers in the presence of at least 200 mM sodium chloride. TT-PME of pure composition requires affinity chromatography treatment. Structural analysis by MALDI-TOF/TOF MS and PCR cloning of TT-PME demonstrated that its sequence is highly distinct from previously described *Citrus* PMEs. The nucleic acid sequence of the gene for this novel TT-PME makes possible the production of recombinant TT-PME.

Multimiligram quantities of the enzyme can now be readily generated for use to determine substrate specificity and action pattern and to evaluate performance for improving functional properties of commercially viable pectins.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the TT-PME protein, operably linked to a promoter and/or other regulatory sequences.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence. (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to TT-PME polypeptide that is substantially free of other proteins, lipids, carbohydrates or other materials with which it is naturally associated. One skilled in the art can purify TT-PME using the techniques for protein purification of the invention. The purity of the TT-PME polypeptide can also be determined by amino-terminal amino acid sequence analysis.

The invention includes functional TT-PME polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of TT-PME polypeptide", refers to all fragments of TT-PME that retain TT-PME activity and function as a thermally tolerant pectin methylesterase. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of TT-PME can be utilized in bioassays to identify functional fragments of TT-PME polypeptide or related polypeptides.

Modifications of the TT-PME primary amino acid sequence may result in further mutant or variant proteins having substantially equivalent activity to the TT-PME polypeptides described herein. Such modifications may be deliberate, as by site-directed mutagenesis, or may occur by spontaneous changes in amino acid sequences where these changes produce modified polypeptides having substantially equivalent activity to the TT-PME polypeptides. Any polypeptides produced by minor modifications of the TT-PME primary amino acid sequence are included herein as long as the biological activity of TT-PME is present; e.g., having pectin methylesterase activity at temperatures higher than that tolerated by TL-PMEs.

A heterologous coding sequence refers to coding sequences which encode peptides or proteins, unrelated to, or, other than, the TT-PME polypeptides provided above and which are not intrinsically found in the position provided in the chimeric gene construct.

Genes encoding a TT-PME protein can be cloned using a variety of techniques according to the invention. The simplest procedure for the cloning of TT-PME genes requires the cloning of genomic DNA from an organism identified as producing a TT-PME protein, and the transfer of the cloned DNA on a suitable plasmid or vector to a host organism which does not produce the TT-PME protein, followed by the identification of transformed hosts to which the ability to produce the TT-PME protein has been conferred. The transforming TT-PME-conferring DNA can be cleaved into smaller fragments and the smallest which maintains the TT-PME-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a TT-PME polypeptide and which hybridize under stringent conditions to the TT-PME sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Sequence alignments and percent identity calculations were performed as described below in BLASTp and BLASTn using default parameters as listed in the 16 Apr. 2007 release.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence, orange. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have TT-PME-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the TT-PME polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, TT-PME activity as described herein. Such variants may result from, for example, genetic polymorphism or from human manipulation. Biologically active variants of a native TT-PME protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired TT-PME activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of TT-PME protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

EXAMPLES

Having now generally described this invention, the same will be better understood by reference to certain specific examples, which are included herein only to further illustrate the invention and are not intended to limit the scope of the invention as defined by the claims.

Example 1

Methods Utilized for Analysis of Protein Preparations

Protein Determination Assay. Protein concentrations were determined according to the method of Lowry et al. (1951. *J. Biol. Chem.* 193: 265-275) using bovine serum albumin as standard. Coomassie blue reagent (Biorad Laboratories, Hercules, Calif.) and the bicinchonic acid reagents (Pierce Chemical Co., Rockford, Ill.) were used to compare determination for purified PME. All determinations were performed according to the standard protocol supplied by the manufacturer. Protein content of purified PME was also determined by absorbance at 280 nm using the extinction co-efficient calculated from the protein composition of the mature protein using the ProtParam program at the ExPASy proteomics tool website (http://au.expasy.org/tools/).

Enzyme Activity Assay. PME activity was determined by pH-stat titration as previously described (Savary et al. 2002, supra) using a TIM 854 autotitrator (Radiometer Analytical, Loveland, Colo.) with 1% *citrus* pectin containing 1.2% sodium chloride maintained at pH 7.0 and 30° C. Enzyme solutions were diluted to give consumption rates of 20-50 µL titrant solution (0.02 M sodium hydroxide) per min. One unit of activity is 1 µmol hydroxide equivalents consumed per minute. Thermally-tolerant PME activity was determined as residual enzyme activity following heat treatment at 70° C. for 10 minutes in a solution of 0.05 M sodium phosphate buffer (pH 7.0) containing 0.1 M sodium chloride (Wicker, L. 1992. *J. Food Sci.* 57:534-535). Polygalacturonase-inhibitor protein (PGIP) activity was determined by the method of Kemp et al. (supra) using Megazyme *Aspergillus* polygalacturonase M2 (Wicklow, Ireland).

Galacturonic Acid Determination. Chemically, pectin is a linear polysaccharide containing from about 300 to 1,000 monosaccharide units. D-Galacturonic acid (GalA) is the principal monosaccharide unit of pectin. Some neutral sugars are also present in the substance. Soluble pectins in pulp extracts and chromatography fractions were determined colorimetrically as galacturonic acid equivalents using a modified meta-hydroxy biphenyl method as described by Kintner and Van Buren (1982. *J. Food Sci.* 47: 756-759). An aliquot (10 µL) of samples (clarified by centrifugation for 10 min at 17,000×g) were diluted to 200 µL with deionized water and cooled in an ice bath for 10 min, after which 1.2 ml of conc. $H_2SO_4$ was added and then vortexed vigorously. Samples were subsequently heated for 5 min at 100° C. and then cooled immediately by placing on ice. Thereafter 20 µL of 0.15% meta-hydroxy biphenyl (prepared in 0.5% NaOH) was added, vortexed immediately, and incubated at RT for 20 min. The absorbance was recorded at 520 nm, and the pectin contents were estimated based on the standard curve with GalA.

Separation of soluble pectinates. Proteins extracted from *citrus* pulp by differential salt-elution were found contaminated by co-solubilized pectinates. TT-PME activity was observed to strongly associate to such pectinates despite the presence of half molar concentration of sodium chloride. This was shown by only partial binding of TT-PME activity when salt-containing cell wall extracts were applied to concanavalin A lectin affinity chromatography media (data not shown) and by incomplete PME activity permeation through a 100,000 NMWL ultrafiltration membrane at pH 5 with 0.5 M and at pH 8.0 with 1.0 M sodium chloride (data not shown). Similar ultrafiltration results were described by Snir et al. (1995). Co-extracted pectinates appear to be pervasive in *citrus* fruit extracts and confound efforts to dialyze or separate proteins by chromatography, even when extracts were previously treated by ammonium sulfate precipitation (Cameron and Grohmann, 1995, supra; Snir et al., 1995; Chen et al., 1998, supra; Corredig et al. 2000, *J. Agric. Food Chem.* 48: 4918-4923). Ammonium sulfate precipitation treatment commonly contributed to large activity losses, and it is an undesirable procedure for large-scale enzyme preparation.

We addressed this by selective removal of soluble pectinates using anion-exchange chromatography in the presence of moderate salt contents. We hypothesized that the pectinates with the greatest charge density were primarily responsible for protein binding interactions in solution, particularly for cationic protein such as PMEs, and would be selectively separated. This was based on Cheng and Kindel's (1995) report that *citrus* polygalacturonic acid was largely retained on anion-exchange resin following washing with 0.5 M sodium chloride. We found that GalA contents in the extract were in fact greatly reduced by simple batch-wise treatment with DEAE-Sepharose after reducing the sodium chloride molarity to 0.2 M by dilution. The 1.93 mg GalA eqs. per mL content in pulp extracts was reduced 25-fold to less than 0.08 mg/ml residual GalA by this treatment. Similar reductions were obtained by treating an extract with Sigma *Aspergillus* pectinase, which could be eliminated by the extended heat treatment at 70° C. (results not shown).

Figure 3:
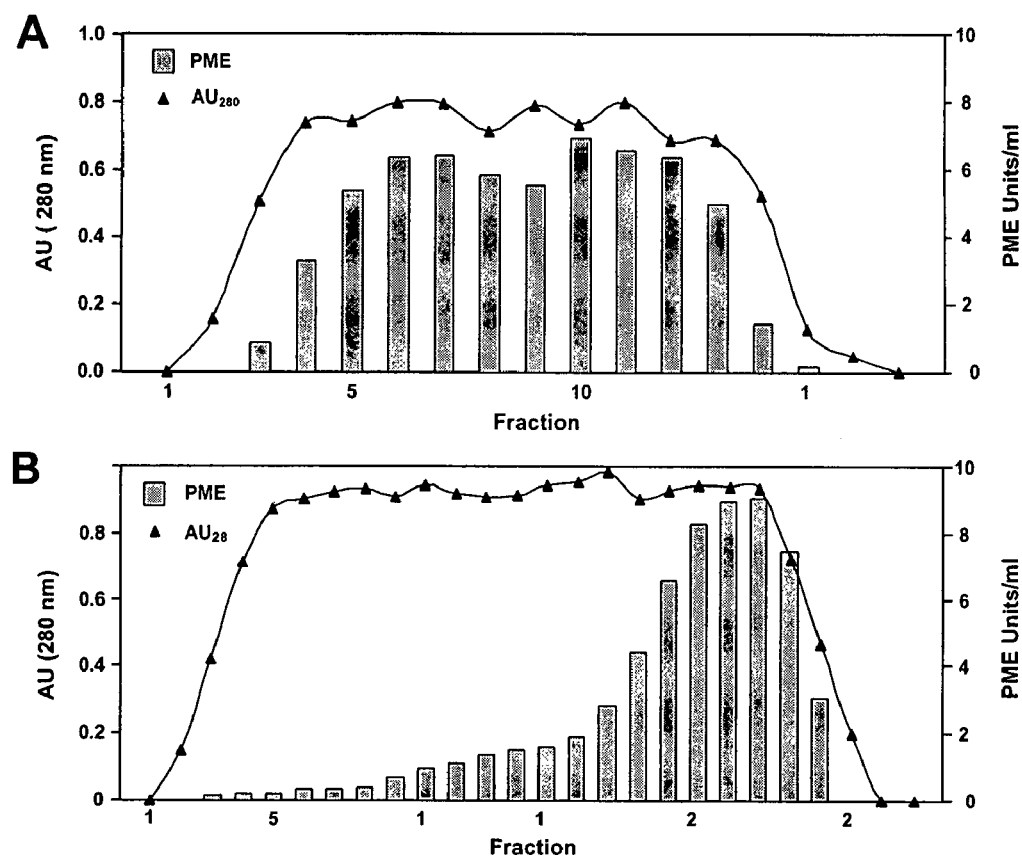
FIGS. 3A and 3B depict the protein and PME activity binding to a PMEIP-Sepharose affinity column. The flow-through fractions of orange pulp extracts applied to column before (FIG. 3A) and after (FIG. 3B) treatment to separate soluble pectinates.

Separation of PME activity by inhibitor protein affinity chromatography. We tested TT-PME binding to a PME-IP-Sepharose affinity column (Denés et al. 2000a. *Carbohydr. Res.* 327:385-393; Denés et al. 2000b. *J. Sci. Food. Agric.* 80:1503-1509) before and after separation of the pectinates with anion-exchange medium. Our detailed evaluation of this column is presented in FIG. 3. Application of untreated finisher pulp extract containing soluble pectinates resulted in PME activity immediately detected in the column flow-through fractions (FIG. 3A). From about 959 PME units passed through the column, 416 units were recovered after elution treatment. Repeating affinity chromatography of finisher pulp extract following removal of the soluble pectinates, negligible PME activity was initially detected in the flow-through fractions (FIG. 3B). Sample was applied until there was a substantial increase of PME activity in the flow-through, which indicated binding capacity of the column was becoming saturated. Following washing with loading buffer, 1323 units were recovered with elution buffer. Upon re-application of the flow-through fractions containing unbound PME activity, all activity was subsequently bound to the column. These results demonstrated that pectinates could interfere with affinity binding in the presence of 0.5 M sodium chloride but that they were effectively eliminated by the anion-exchanger pretreatment. Removal of pectinates allows extracts to be applied directly in subsequent chromatography treatments without requiring dialysis or precipitation steps, providing a simplified treatment for processing large volumes of sample.

No PGIP activity was detected in the bound-protein fraction eluted from the PME-IP affinity column, but was observed only in the flow-through volume. This confirmed the different heat-inactivation profiles suggesting that TT-PME and PGIP were two different proteins. Their separation requiring specific protein-protein binding selectivity therefore indicates these two proteins have highly similar physical-chemical properties that have resulted to their co-isolation in several independent isolation studies (for both PGIP and PMEs). We report the complete purification and structural characterization of the orange PGIP in a separate study (Prasanna et al., manuscript in preparation).

Electrophoresis Methods. SDS-PAGE was performed as described previously (Cameron et al., 2005, supra) using a NuPAGE Novex 12% Bis-Tris gel (Invitrogen, Carlsbad, Calif.) with MOPS buffer following the manufacturer's instructions. Gels were calibrated with Mark-12 wide range unstained protein standards or SeeBlue Plus2 pre-stained protein standards and stained with Simply Blue Coomassie G-250 staining according to the instruction manual. Samples were routinely prepared for PAGE by precipitation with 7.5% TCA precipitation as described by Peterson (1977, *Anal. Biochem.* 83, 346-356).

Approximately 1.0 µg of each PME was loaded onto gels. For N-terminal protein sequencing, TT-PME bands were resolved on a 10% SDS-PAGE gel and electroblotted to Biorad Trans-Blot PVDF membrane in CAPS buffer as previously described for orange PMEs (Savary et al. 2002, supra). Direct N-terminal amino acid sequencing of blotted proteins was performed with an Applied Biosystems Procise 491 protein microsequencing system. Initial yields averaged 5 pmol per cycle.

Example 2

PME Extraction Trials

Sweet orange finisher pulp (*Citrus sinensis* cv. Hamlin or Valencia) was obtained from Citrus World (Lake Wells, Fla.) and stored frozen at −20° C. prior to use. Aliquots of approximately 10 g of finisher pulp were extracted with different buffers (1:3, w/v) and sodium chloride concentrations to determine effective conditions for scaled-up TT-PME isolation. All chemicals and solvents were of analytical grade and purchased from Sigma-Aldrich Chemical Company (St. Louis, Mo.), unless otherwise specified. Extractants used were either water without adjustment to endogenous pH of pulp slurry (pH 3.6) or buffered solutions containing either 0.1 M Tris-HCl, pH 8.0 or 0.02 M sodium acetate, pH 5.0, containing varying sodium chloride content (0.0, 0.1, 0.5 or 1.0 M). Since no soluble PME activity was detected in salt-free water extracts, the finisher pulp was washed with water until a clear-running solution was obtained, and then this treated pulp was used for extraction treatments. Extractions were performed by combining tissue and extraction solution in 50 ml centrifuge tubes and incubating for at least 1 hr with intermittent vortexing and sonication. Following centrifugation (Sorvall SS-34 rotor, 20 min at 20,000 rpm; Dupont Instruments, Doraville, Ga.) the supernatants were tested for soluble PME activity. Total and TT-PME activities as well as protein concentrations were determined before and after heat treatments.

Fruit PMEs and PGIPs are cell wall-associated proteins and their effective purification can be improved by washing tissue prior to salt elution. Differential extraction of TL-PME and TT-PME activities by pH and salt contents was observed previously (Wicker, 1992, supra). FIG. 1 compares recoveries of PME activities from orange finisher pulp with acetate (pH 5.0) and Tris (pH 8.0) buffers and addition of 0.5 or 1.0 M sodium chloride. As expected, PME activity remained tightly associated with pulp tissue extracted with water only (this slurry measured at pH 3.8). TT-PME was readily solubilized with elevated pH, with about a doubling of activity eluted with sodium chloride. TL-PME activity is much more sensitive to pH and salt contents, with highest yields at pH 8.0 and 1.0 M sodium chloride. These results are comparable with previous results for PME extraction from Marsh grapefruit pulp showing differential solubility between TL- and TT-PME activities (Wicker, 1992, supra). Extraction at the lower pH 5.0 (acetate buffer) with 0.5 M sodium chloride was selected since this provided for enriched TT-PME activity, while reducing co-extracted total protein and TL-PME activity. This pH and salt content would also allow for direct application of filtered extract to affinity chromatography media without major manipulations such as dialysis and ammonium sulfate precipitation, thus eliminating previously observed excessive losses of enzyme activity.

Figure 2:
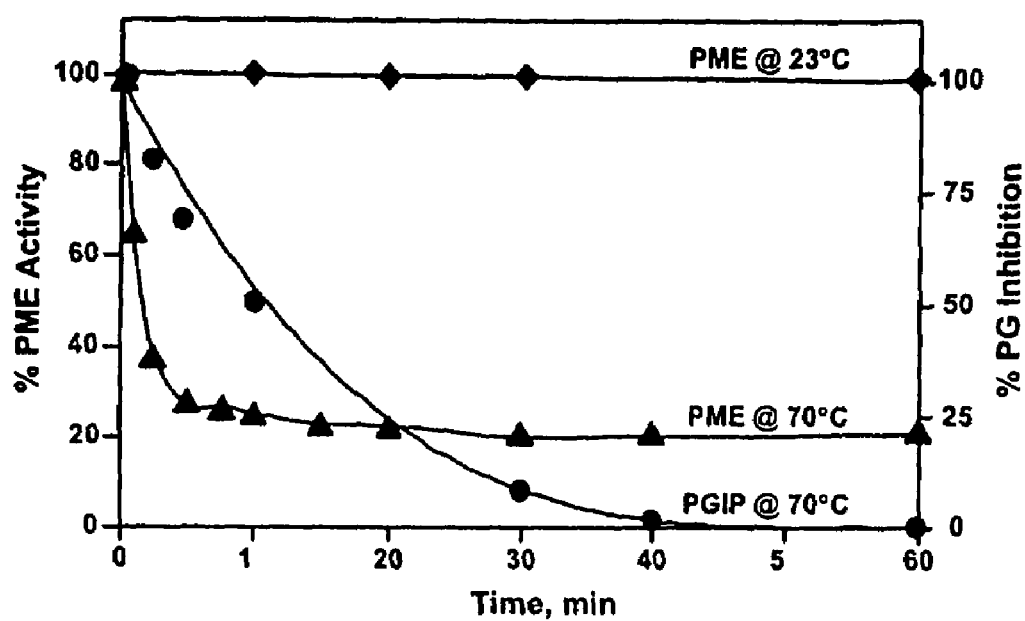
FIG. 2 depicts the inactivation of enzyme activity in orange finisher pulp extract induced by a 70° C. heat treatment over a time course of 60 min.

Our previous analyses (Cameron et al., 1995, Cameron and Grohmann, 1996, supra; Cameron et al., 2005, supra) showed an association of the monocomponent TT-PME preparation with N-terminal peptide sequences having high sequence identity with grapefruit and orange PGIPs. PGIPs have been reported to have thermal stability by others (Deo and Shastry. 2003. *Plant Sci.* 164: 147-156; Sicilia et al. 2005. *Plant Physiol.* 139: 1380-1388). Thermostability curves were determined for the orange finisher pulp extract for both PME and PGIP activities. Testing at 70° C. over 60 min (shown in FIG. 2) revealed two distinct stability profiles. Total PME assay showed rapid inactivation of the TL-PME component with heat treatment at 70° C., with better than 95% activity eliminated within 10 min, while the TT-PME component (20% of initial PME activity) remained stable through 60 min of treatment. Snir et al. (1996, supra) and Vercet et al. (1999. *J. Agric. Food Chem.* 47: 432-437) reported similar stability TT-PME activity. PGIP activity showed modest thermal stability profile, with 50% activity remaining after 10 min incubation, but this activity was nearly eliminated after 40 min. Such differences in thermostabilities for TT-PME and PGIP activity suggest they are not likely represented by a singe protein. Extended heat treatment of at least 40 min may therefore be useful in large-scale preparation of monocomponent TT-PME activity.

Example 3

Preparative Purification of TT-PME

Figure 4:
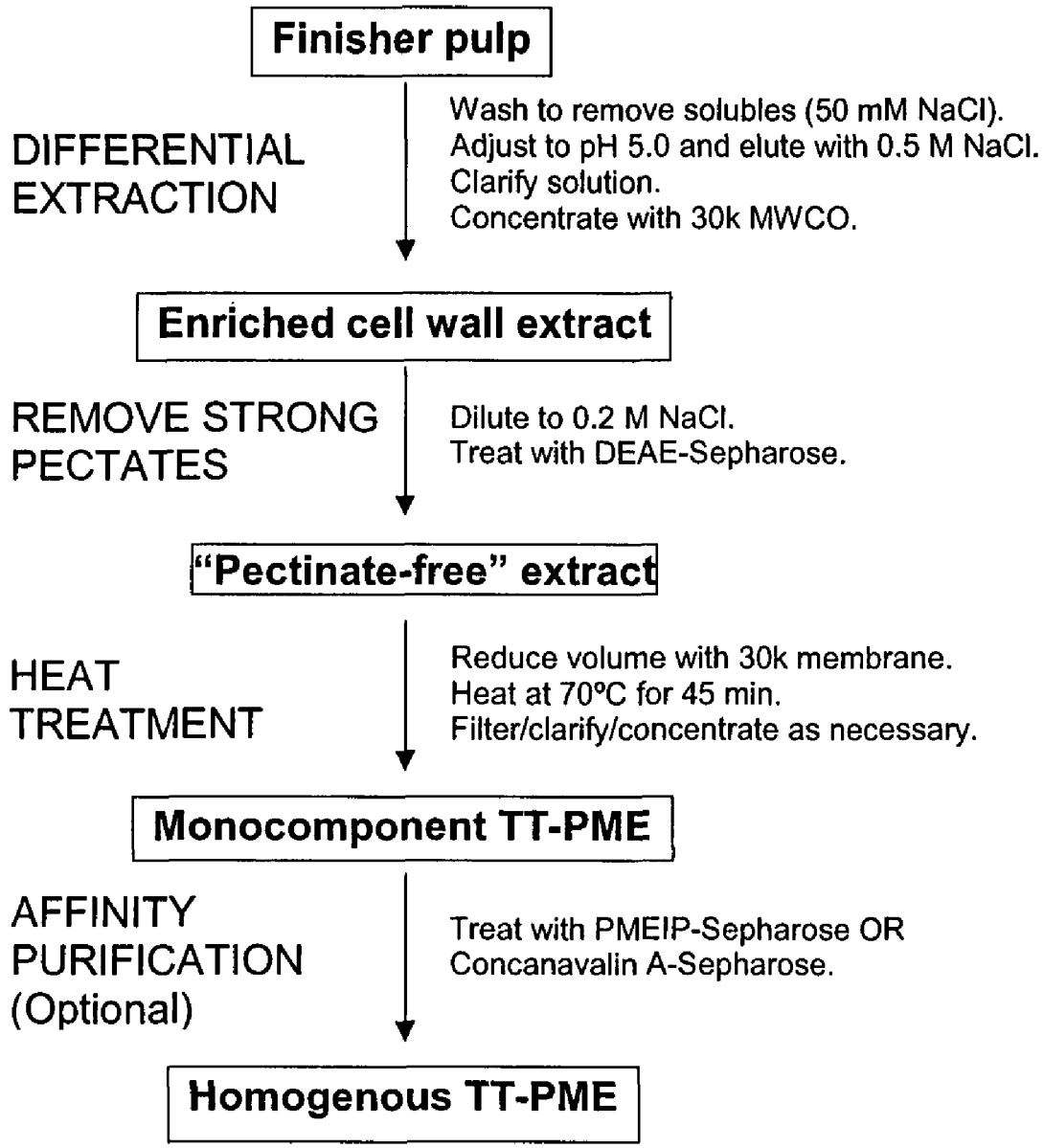
FIG. 4 shows a diagram depicting a simple, direct method for high-yield TT-PME preparation.

A full-scale preparative purification of TT-PME from finisher pulp was processed (FIG. 4) combining ultrafiltration, heat treatment, differential adsorption of pectinates by anion-exchange chromatography, and selective affinity-binding to immobilized PME-IP. Preparative extraction of washed finisher pulp (1.3 kg) for TT-PME purification was performed with 0.02 M acetate buffer containing 0.5 M sodium chloride. Thawed finisher pulp was washed 5 times (2 hrs each treatment) with 4.5 L water containing 0.05 M sodium chloride (resulting in a clear-running final filtrate). The washed pulp was extracted overnight at 4° C. with continuous stirring using 4.5 L of 0.02 M sodium acetate containing 0.5 M sodium chloride and 0.02% sodium azide, and adjusting to pH 5. with sodium hydroxide. The extract was filtered through two layers of Miracloth (Calbiochem) and clarified by centrifugation at 8000 rpm (Sorvall SLC-6000 rotor) for 40 min (4° C.). Suspended particulates were removed by filtration with Gelman GF pre-filters under low vacuum. The extract was then concentrated by tangential-flow ultrafiltration using a 30,000 NMWL regenerated cellulose membrane (Millipore, Bedford, Mass.). The retentate was diluted with deionized water to reduce the sodium chloride concentration to 0.2 M and then re-concentrated. Sodium phosphate monobasic was added to bring solution to 0.02 M and then adjusted to pH 7.0 with NaOH. This solution was heated to 70° C. in a waterbath for 40 min, then cooled on ice for 1 h, and finally centrifuged at 15,000 rpm (Sorvall SLA-1500 rotor) for 40 min to clarify the solution.

The clarified heat-treated extract was subsequently treated with DEAE-Sepharose to remove co-extracted soluble pectins having relatively high charge density (i.e., pectinates). DEAE-Sepharose was pre-conditioned to pH 7.0 batch-wise in a beaker following manufacturer's recommendations. The extract solution was treated in portions (150 ml) by mixing with the DEAE-Sepharose (ca. 150 ml settled bed volume) in a 2 L beaker, maintaining pH 7.0, then recovered with a fine glass-frit Buchner funnel. The adsorbent was treated once with buffer solution. This wash and the extract were combined and concentrated by ultrafiltration (30,000 NMWL YM membrane in an Amicon stirred-cell) and finally clarified by centrifugation. Sodium chloride was added to return the solution to 0.5 M.

PME activity was separated using a PME-IP affinity chromatography column (7.5 ml bed volume with binding capacity of ca. 14,000 PME units) prepared following methods described by Denés et al. (supra). The affinity column was pre-equilibrated with 0.002 M phosphate buffer (pH 7.0) containing 0.5 M sodium chloride, and the bound TT-PME was eluted with 0.020 M carbonate buffer (pH 10.0) containing 1.0 M sodium chloride. The TT-PME containing solution was immediately neutralized and concentrated to at least 1 mg/ml with an Amicon Centricon-10. This sample was exchanged into sodium phosphate buffer (pH 7.0, 0.1 M) using a Biorad Econopak 10DG de-salting column and re-heated at 70° C. for at least 20 min, followed by centrifugation. The final preparation was stored with 0.02% sodium azide (w/v) at 4° C.

The purification results are summarized in Table 1. TT-PME initially represented 43% of total PME activity extracted from 1.3 kg wet pulp. It was purified 163-fold with a yield of 72% to provide 8 mg of purified protein with specific activity of 963 units/mg protein (protein determined by Lowry method). This result represents a better than a 10-fold improvement over prior reports for any orange PME purification.

Figure 5:
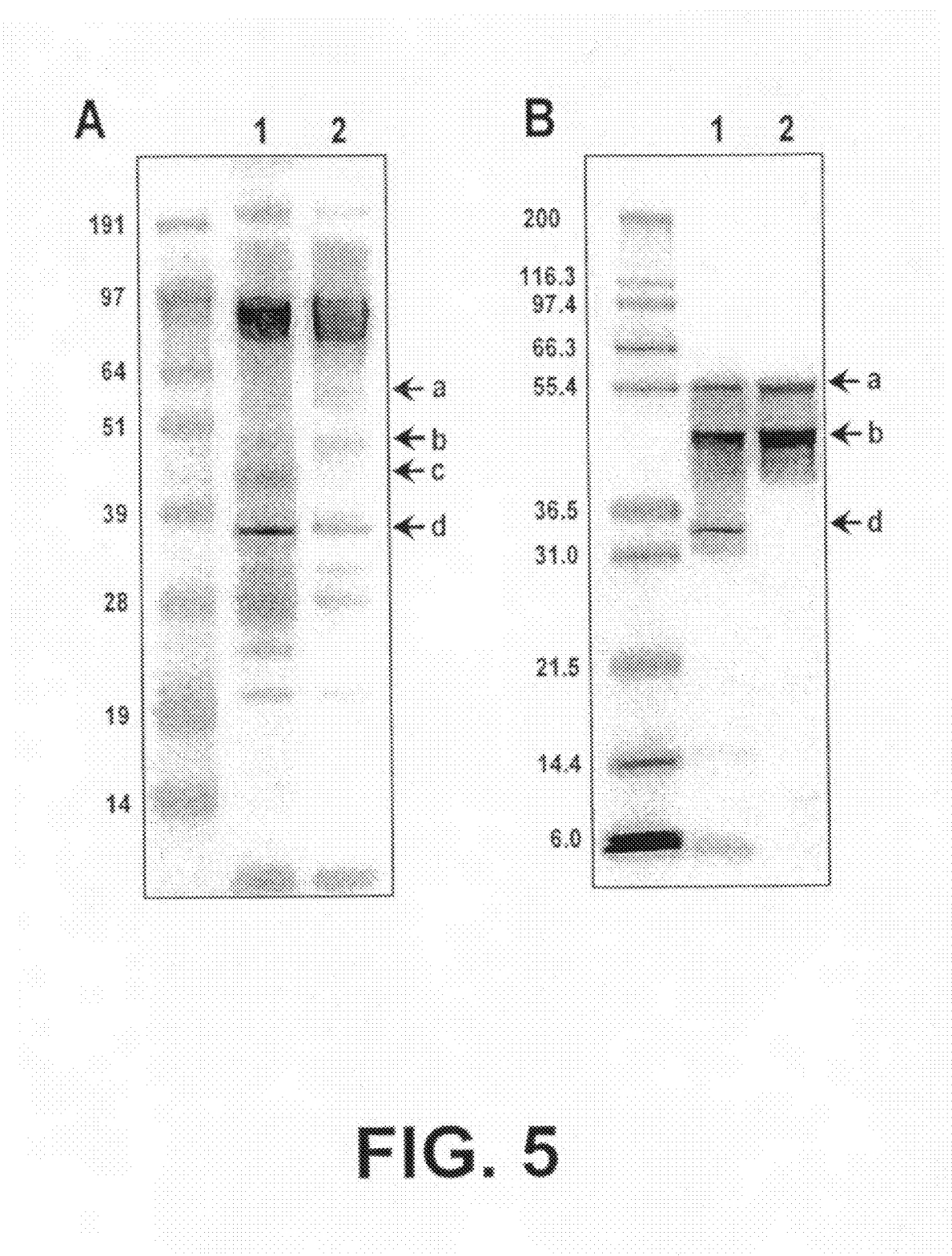
FIGS. 5A and 5B depict the evaluation of protein preparations by SDS-PAGE.

Assessment of protein purity by SDS-PAGE is shown in FIG. 5. Two pairs of doublet bands were observed with molecular masses estimated at 55.3 kDa and 56.5 kDa and 46.0 kDa and 47.2 kDa. Two bands were resolved in the 56 kDa band in separate experiments by differential binding to Con-A Sepharose and by running a 10% PAGE gel (results not shown). Thus, the purified TT-PME isolated and purified by the purification strategy of the invention and analyzed by SDS-PAGE represents a novel TT-PME based on its molecular mass.

As discussed above, in a previous report describing TT-PME activity (Cameron et al., 2005, supra), we associated TT-PME activity with a diffuse 40.8 kDa band. In this study, a dominant protein of that approximate size was shown to be eliminated by heat treatment and separated by PME-IP affinity chromatography; it was found only in unbound flow-through fraction. MALDI-TOF MS analysis confirmed its identity as PGIP protein (Prasanna et al., manuscript in preparation). Thus, the previously identified ~41 kDa protein is not a TT-PME.

Figure 6:
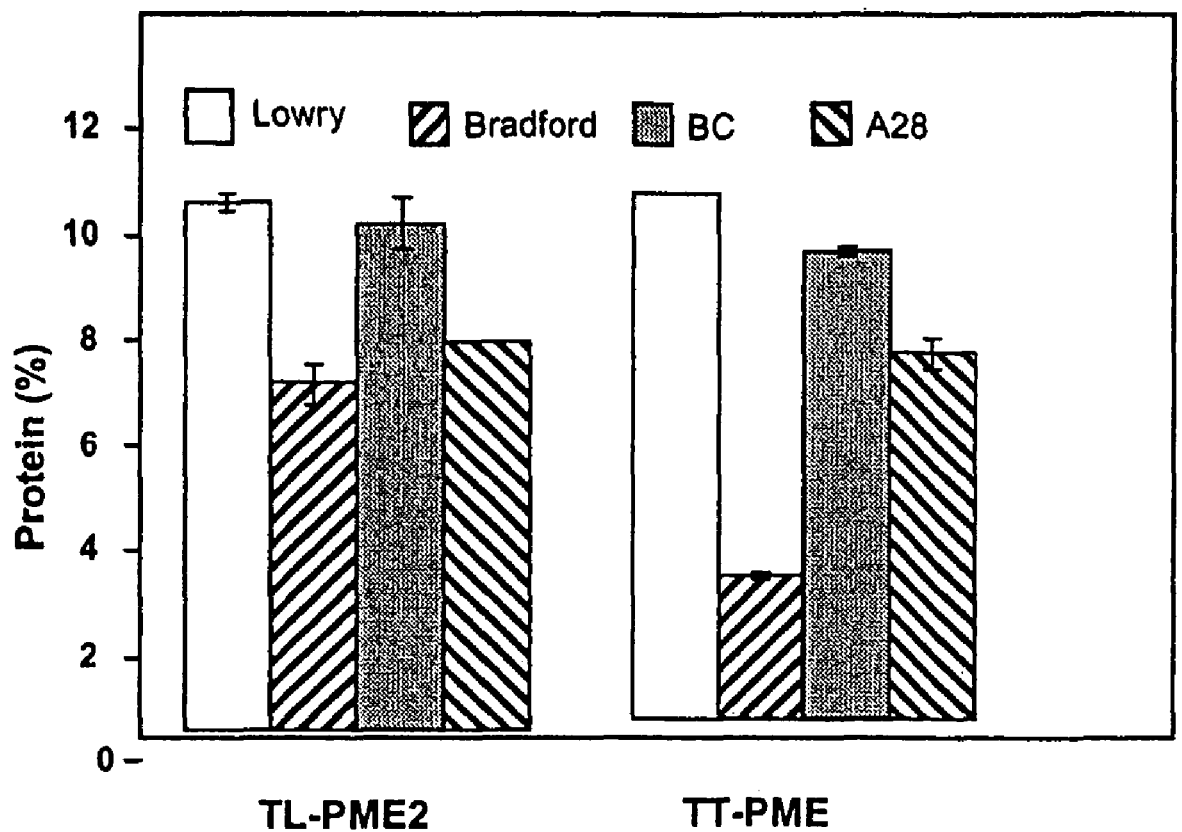
FIG. 6 shows a comparison of protein determination methods for TT-PME. The assay was performed with affinity-purified protein.
Figure 7:
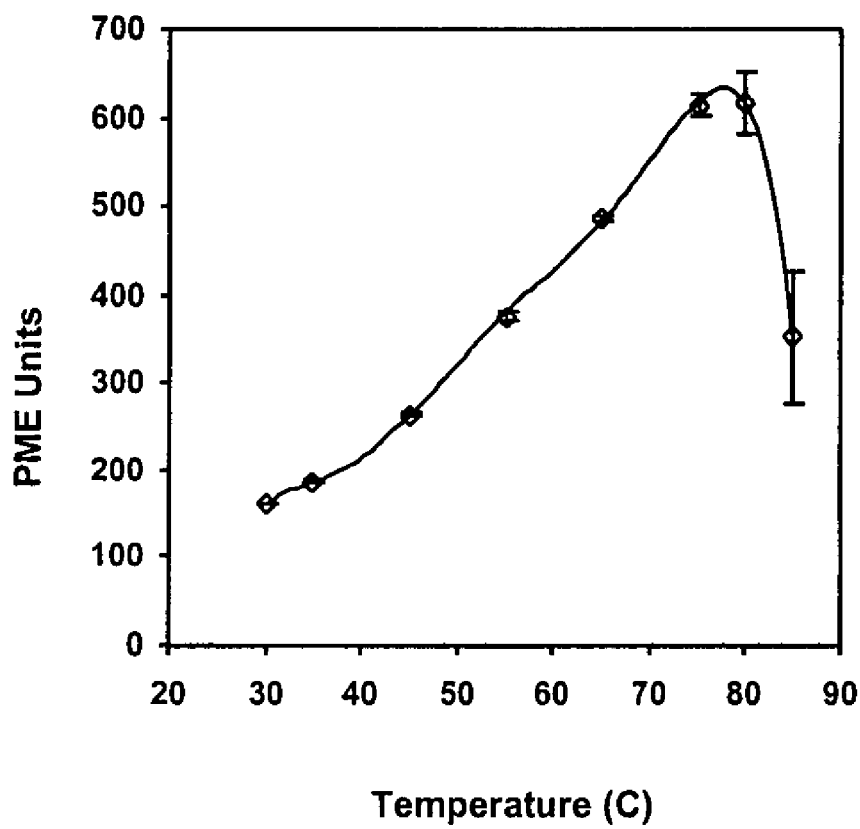
FIG. 7 depicts the determination of the optimal temperature for TT-PME activity. Purified TT-PME was assayed using standard pectin treatment conditions while varying the temperature.

With this purified TT-PME preparation we measured specific activity with different protein determination methods and examined activity patterns with standard pectins. FIG. 6 shows TT-PME protein determination in comparison with pure TL-PME2. Lowry method is more sensitive for both PMEs, which will result in a lower specific assay compared to the Bradford reagent. Calculating TT-PME activity with the Bradford reagent gives a specific activity of 1600 U/mg, which is similar to purified TL-PME2 (Savary et al. 2003, supra). Sodium chloride and pH-dependant activity profiles determined with this pure TT-PME preparation were identical to our previous report (Cameron et al., 2005, supra) (results not shown). Optimal activity was determined at pH 5.5-9.5 in the presence of 0.2 M NaCl and pH 7.0 and greater with lower NaCl concentrations. The optimal temperature for TT-PME activity was about 75° C.; the TT-PME showed substantial activity at 45°-85° C. under standard pectin treatment conditions (FIG. 7). TT-PME activity was measured on two commercial lemon pectins under possible process conditions (pH 5.5 and 45° C.) and compared to standard activity determination. The results in Table 2 show pectin can be treated at elevated temperature to increase activity that would otherwise be reduced by treatment at suboptimal pH. We are inves-

TABLE 1

Purification of TT-PME from commercial finisher pulp.*

| Treatment | Volume (ml) | Protein (mg) | Total (units) | TT-PME (units) | Specific Activity | Purification | Recovery (%) |
|---|---|---|---|---|---|---|---|
| Cell wall extract | 4328 | 1808 | 24,341 | 10,658 | 5.9 | 1.0 | 100.0 |
| 30,000 NMWL concentrate | 206 | 883 | 21,521 | 10,004 | 11.3 | 1.9 | 93.9 |
| Heat, DEAE - Mono-competent | 134 | 141 | 9,173 | 9,173 | 65.0 | 11.0 | 86.0 |
| PME-IP Affinity - homogeneous | 5.6 | 8.0 | 7,711 | 7,711 | 962.6 | 163.4 | 72.3 |

*Extraction from 1.3 kg of washed pulp. Protein determined by Lowry method.

tigating separately the pH influences on action patterns by TT-PME for comparison with the TL-PMEs.

Thus, the TT-PME of the invention can be used to treat pectin-containing plant material to reduce the viscosity or to improve processing or appearance of plant material and the treatments can be performed at room temperature or at elevated temperatures up to about 85° C.

Further, treatment of pectin with the TT-PME of the invention was shown to produce a block demethylated pectin that contains an ordered intramolecular distribution of blocks of contiguously demethylated galacturonic acid subunits within many, or all, of the population of pectin molecules (data not shown).

TABLE 2

Comparison of TT-PME activity with two commercial pectins and process conditions.

| Pectin Type | Assay conditions (units ± S.D.) | |
| --- | --- | --- |
| | pH 7.0; 30° C.[1] | pH 5.5; 45° C. |
| Citrus | 1588 ± 39 | 2043 ± 30 |
| Lemon #1328* | 1599 ± 29 | 2046 ± 31 |
| Lemon #1329 | 1561 ± 17 | 1081 ± 11 |

[1]Standard assay conditions using Sigma Citrus pectin
*Commercial lemon pectins Example 4

Amino Terminus Sequence Characterization

Electrophoresis analysis of purified TT-PME. The sequence obtained was subsequently used for BLASTp searching of the non-redundant plant database (www.ncbi.nlm.nih.gov/) and the Plant Genome Central Large Scale *Citrus* EST Sequencing Project database (http://www.ncbi.nlm.nih.gov/genomes/PLANTS/PlantList.html) at the National Center for Biotechnology Information website.

N-terminal peptide sequences were generated directly from the four size variants in the TT-PME preparation. We obtained a single identical 18 amino acid sequence from the four proteins: L-Q-K-S-V-X-L-T-K-F-D-L-I-V-A-V-K-D (SEQ ID NO:3). These results demonstrate the four TT-PME size variants are processed from a pro-peptide at a common cleavage site during biosynthesis and secretion. The variation in TT-PME size is presumable due to differences in glycosylation. The 45-46 kDa pair showed consistently strong binding to Con-A Sepharose, while the 56-57 kDa pair showed variable weak binding. The later pair may contain modified glycans having extended sugar moieties that result in the observed reduced affinity by the lectin.

Screening of the TT-PME N-terminal peptide by BLAST search (Altschul et al. 1997. *Nucleic Acids Res.* 25: 3389-3402) at the NCBI website did not match any *Citrus* PME sequence in the non-redundant database. Results also gave no significant scores to suggest relationship to PMEs. These results thus indicated this was a newly discovered form of PME. Further searching of the translated PlantEST BLAST database (three frames and both directions) for *Citrus sinensis* sequences deposited from the Large-Scale EST Sequencing Project at NCBI resulted in matching two accessions, CK936641 obtained from developing fruit flavedo cDNA, and CF833608 obtained from ovary tissue at anthesis. Identical sequences were also present in three *C. clementina* EST cDNAs generated from reproductive and vegetative tissues. Accession DY285162 from *C. clementina* provided the longest EST nucleotide sequence of all *Citrus* EST matches. In each translated *Citrus* EST sequence, the undesignated residue (X) in the TT-PME N-terminal peptide corresponded to asparagine. This residue is likely glycosylated since no amino acid was evident in that sequencing cycle in TT-PME protein and it is present as an N-X-T sequon.

Example 5

MALDI-TOF/TOF Mass Spectrometry and Peptide Sequence Analysis

Samples were prepared for MALDI-TOF/TOF MS as described recently for other orange PMEs (Savary et al., 2007). Coomassie blue-stained protein bands were excised from the SDS-PAGE gels, digested with Trypsin Gold (Promega, Madison, Wis.), and the extracted peptides were recovered from Millipore C18 Zip Tips using 60% acetonitrile—0.1% TFA containing α-cyano-4-hydroxycinammic acid matrix prior to spotting a mixture with a saturated matrix solution [α-cyano-4-hydroxycinnamic acid in 0.1% TFA/acetonitrile (70:30, v/v)] on the target plate. MS and MS/MS spectra were acquired with a 4700 Proteomics analyzer (Applied Biosystems, Framingham, Mass.) and evaluated with the MASCOT search engine associated with the GPS Explorer program. De novo peptide sequences for eight of the tryptic peptides was accomplished by MS/MS spectrum interpretation using PEAKS (Bioinformatics Solutions Inc., Waterloo, Ontario, Canada) automatic de novo algorithm software (Ma et al. 2003. *Rapid Comm. in Mass Spectrom.* 17: 2337-2342), with the following parameters: precursor ion mass tolerance 0.05 Da, fragmented ions mass tolerance 0.1 Da, and trypsin as digestion enzyme. Oxidized methionine was selected as a variable modification and de novo sequences carrying methionine where verified versus the detection of the oxidized/not-oxidized ion in the MS spectrum for additional confirmation. Guanidination reagent (Sigma-Aldrich, MS0100) was used to confirm assignments between Q and K for internal positions. Each peptide was subsequently used for BLAST search of the non-redundant protein and *Citrus* EST databases as performed for the N-terminal peptide sequence.

Figure 8:
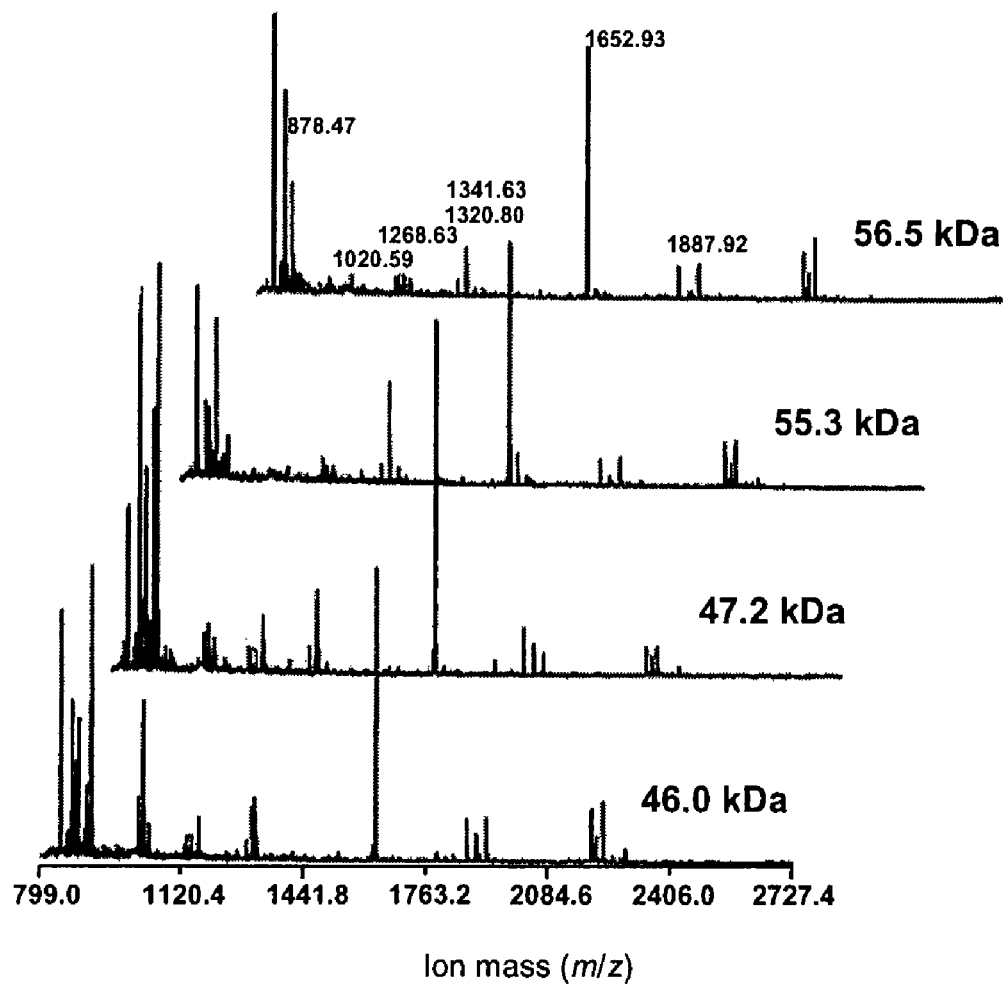
FIG. 8 depicts MALDI-TOF MS mass spectra (800 to 2727 m/z) of trypsin digests from four TT-PME proteins resolved by SDS-PAGE. Masses of seven common peptide ions that provided MS/MS spectra suitable for de novo sequencing are indicated above the upper spectrum.
Figure 9:
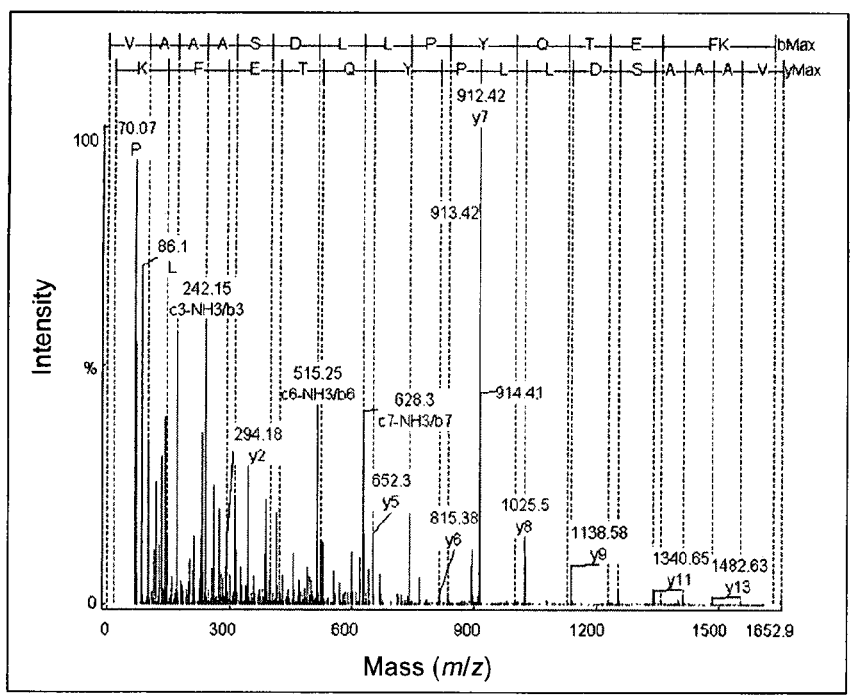
FIG. 9A shows common peptides present in the four TT-PME proteins and amino acid sequences determined by MS/MS. Those peptides sequences not determined (N.D.) directly were subsequently matched from the translated TT-PME nucleotide sequence.
FIG. 9B depicts the mass spectrum from MS/MS demonstrating de novo sequencing of peptide 1652.85.

The four TT-PME bands resolved by SDS-PAGE were each trypsin digested and evaluated by MALDI-TOF MS. Consistent with a common N-terminal peptide, a common peptide mass fingerprint was observed for them (FIG. 8). Twelve significant peptide ions (masses summarized in FIG. 9A) were consistently observed. Automated MASCOT evaluation of the spectra provided protein scores suggesting relationship to rice and orange PME sequences, but TT-PME did not match with any known *Citrus* PME sequence in the non-redundant database. Further investigation of the common peptides by MALDI-TOF/TOF MS resulted in high confidence determination of de novo sequences for 8 peptides. The MS/MS spectrum representing the base-ion, mass 1652.85 Da, is shown in FIG. 9B. An observed 794.46 Da peptide best fitted the sequence HQAVALR, which is a common peptide observed in TL-PMEs (Savary et al., 2007) and is present in a highly conserved sequence region in plant PMEs (Markovič and Janeček. 2004. *Carbohydr. Res.* 339: 2281-2295; Pelloux et al., supra).

Example 6

Sequence Analysis

The TT-PME tryptic peptides were overlaid with alignment of three translated amino acid sequences from *Citrus*

EST cDNAs that were initially identified with the N-terminal peptide. Using at least two overlapping peptide or translated nucleotide sequences to establish likely sequence, a common 232 amino acid polypeptide (FIG. 10) was obtained that overlapped part of the pro-peptide and mature protein sequences. In addition to the N-terminal peptide, 5 peptides determined by MS/MS were contained in the three translated EST sequences. Two tryptic peptides that were unambiguously sequenced [TMLMFVGDGIGK (SEQ ID NO:4) and SATVAWGTGFIAK (SEQ ID NO:5)] were used for BLAST search of translated PlantEST sequence database. They were both able to identify the three *Citrus* EST accessions originally identified by the N-terminal peptide. The common 591 nucleotide base sequence from all three *Citrus* EST sequences was used for selecting primers (Table 3) for RT-PCR experiments and for subsequent RACE-PCR experiments to generate the full-length cDNA sequence for TT-PME.

TABLE 3

RT-PCR Primers

| Primer | 5'-3' Sequence | |
|---|---|---|
| PME3A: 100F | CCAGCATTGGACAGAGTTAC | SEQ ID NO: 6 |
| PME3A: 963R | AATCAACGGTGCCATATACG | SEQ ID NO: 7 |
| PME3A: 689R | TCCCATCTCCTACGAACATC | SEQ ID NO: 8 |
| PME3B: 298F | TTGATGGGTTCGCTTACAGT | SEQ ID NO: 9 |
| PME3B: 723R | ACGCTTCTATTGGCCTTCAC | SEQ ID NO: 10 |

Example 7

Cloning of *Citrus* TT-PME

Specific PCR primers (Table 3) were initially used in combination with *Citrus reticulata* 'Clementine' DNA to conduct PCR. DNA was extracted from leaf tissue following the protocol of Dellaporta et al. (1983. *Plant Mol. Biol. Reptr.* 1: 19-21). Three primer combinations were used: PME3A-100F/963R, PME3A-100F/689R, PME3B-298F/723R. Amplicons generated from these primer combinations were sequenced by the dideoxy chain termination reaction (Sanger et al. 1977. *Proc. Natl. Acad. Sci. USA* 74: 5463-5467) using an ABI PRISM Big Dye Termination Cycle Sequencing Ready Reaction Kit (Applied Biosystems) and an automated fluorescent DNA sequencer (Model 3730XL, Applied Biosystems). DNA sequences were analyzed using Sequencher software (GeneCodes, Ann Arbor, Mich.) and BLASTn at the NCBI. Amplicon sequences were found to be identical to sequence contained within NCBI accession DY285162, but containing an 81 base pair intron. Next, primer pairs PME3A-100F/698R and PME3B-298F/732R were used in combination with *Citrus paradisi* 'Marsh' total RNA (prepared from whole immature fruit, ca. 90 days after anthesis) for RT-PCR using the Titan One-Step RT-PCR kit (Roche Diagnostics, Indianapolis, Ind., USA). Total RNA was isolated using the method of Strommer et al. (1993. In: *Methods in Plant Molecular Biology and Biotechnology*, Glick and Thompson, eds. CRC Press, Boca Raton, pp. 49-66). The two RT-PCR amplicons were sequenced as described above and found to be identical to sequence contained within NCBI accession DY285162. Based on this sequence, gene specific primers were designed (Table 4) for subsequent RNA ligase mediated rapid PCR amplification of cDNA ends (RLM-RACE PCR, FirstChoice® kit, Ambion, Austin, Tex.) to generate a full-length cDNA clone of the TT-PME gene. To obtain the complete cDNA encoding the pre- and pro-peptide sequences, the gene-specific primers (5' GS outer primer and 5' GS inner primer for 5' RACE and 3' GS outer primer and 3' GS inner primer; Table 2) were used for RLM-RACE. PCR-RACE amplicons (ca. 700 bp for the 5' amplicon and ca. 1000 for the 3' amplicon) were purified from agarose gels following electrophoresis using the QIAquick gel extraction kit (Qiagen, Md.) and cloned into *E. coli* (TOPO Top10F' cells, Invitrogen, Carlsbad, Calif.). The RACE amplicons were sequenced and analyzed as described above. By combining sequence obtained from the 5' and 3' RACE, a putative full length coding sequence for the TT-PME was obtained. This process was repeated with genomic DNA and fruit mRNA isolated from *Citrus sinensis* 'Hamlin'.

TABLE 4

RACE-PCR Primers

| Primers | 5'-3' Sequence | |
|---|---|---|
| 3' GS Outer Primer 1 | GGCTTATTTTGAGAACGTGGA | SEQ ID NO: 11 |
| 3' GS Outer Primer 2 | GGATCGGCAAAACAGTAGTGA | SEQ ID NO: 12 |
| 5' GS Inner Primer | TCCCTCACGTTTCCGTCACTGT | SEQ ID NO: 13 |
| 5' GS Outer Primer | TCACCGGGGATTTTCTTGAGCA | SEQ ID NO: 14 |

The nucleotide and translated amino acid sequence obtained for *Citrus sinensis* is presented in FIG. 11. It represents a 33 amino acid signal peptide, 212 amino acid propeptide, and 324 amino acid mature protein. The calculated molecular weight for the mature protein is 35,629.4 with a pI of 9.18. There are 23 theoretical tryptic peptides with masses greater than 600 (FIG. 12). Sequencing by MALDI-TOF/TOF MS resulted in 28% coverage of the mature protein. All peptide sequences determined directly by MS/MS, except for one with mass 1341.63 were confirmed from the translated nucleotide sequence. Amino acid substitutions at the N— and C-terminal residues identified by MS/MS (KAYFEN-VEVSR; SEQ ID NO:15)and AGAYFENVEVDK; SEQ ID NO:16) contained accumulated mass differences of 0.04 Da for this peptide, which was within the tolerance limit set for the PEAKS interpretation of experimental MS/MS data. In this case direct inspection of the spectral data did not distinguish the differences (though the MS/MS designation required a "missed cleavage" at lysine). Overall, however, MALDI-TOF/TOF MS sequencing of tryptic peptides generated several peptides that were sufficient to correlate identity to other plant PMEs in sequence databases and to readily identify translated nucleotide sequences for homologous EST fragments that could be used to generate the full nucleotide sequence by PCR techniques.

Sequence elements observed in TT-PME indicate it falls within clade 1 of plant PMEs (Marković and Janeček, supra). Evidence for this are the five conserved cysteine residues and the 14 amino acid sequence ending with the RKLL stretch, which is the putative target for subtilisin-like serine protease in processing the propeptide (Pelloux et al., supra). The relationship of the TT-PME sequence with other plant PMEs was evaluated by further BLAST analysis. Summary of results from the full protein-coding 1710 nucleotide sequence identified the mung bean (*Vigna radiata*) alpha-PME having the highest matching score in the existing non-redundant sequence database. The Vigna sequence provides only 48% coverage, but this may reflect that the cDNA generated covers the mature protein only. It is not known if this represents a Group 1-type PME structural motif (Pelloux et al., supra). Protein BLAST of the TT-PME mature protein sequence similarly indicates a high sequence matching for the *Vigna* PME. Interestingly, TT-PME shows higher overall identity to individual *Oryza* and *Arabidopsis* PME isoforms than the three published *Citrus* PME sequences corresponding to an ethylene-inducible PME (Nairn et al., supra) and two isoforms (Christensen et al. 1998, supra; Nairn et al., supra; Arias and Burns, supra) that correspond to the fruit TL-PMEs, PME2 and PME4 (Savary et al., 2007, supra). TT-PME is therefore demonstratively distinct from previously described *Citrus* PMEs as evidenced by structure and sequence properties.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated or recombinant nucleic acid molecule wherein said nucleic acid molecule encodes a pectin methylesterase polypeptide comprising the amino acid sequence set forth in SEQ ID NO:2, said polypeptide having stability under harsh reaction conditions comprising a pH range of about 3.5 to about 9.5 and a temperature range from about 45° C. up to about 85° C.

2. The isolated or recombinant nucleic acid molecule according to claim 1, wherein said nucleic acid molecule comprises a nucleotide sequence identified by SEQ ID NO: 1.

3. An isolated or recombinant nucleic acid molecule, wherein said nucleic acid molecule comprises a nucleotide sequence that comprises the complement of any one of the nucleotide sequences of claim 1 or 2.

4. The isolated or recombinant nucleic acid molecule of any one of claim 1 or 2, further comprising one or more regulatory elements operatively linked to said nucleic acid.

5. A DNA construct comprising the nucleic acid molecule of claim 1, wherein said nucleotide sequence is linked to a promoter that drives expression in a host cell.

6. A DNA construct comprising the nucleic acid molecule of claim 2, wherein said nucleotide sequence is linked to a promoter that drives expression in a host cell.

7. A vector comprising the DNA construct of claim 5.

8. A host cell comprising the vector of claim 7.

9. The host cell of claim 8, wherein said host cell is a single-celled or lower or higher multi-celled organism into which the construct according to the invention can be introduced wherein expression of said construct results in the production of pectin methylesterase polypeptide comprising the amino acid sequence set forth in SEQ ID NO:2.

* * * * *

SEQUENCE LISTING

<160> NUMBER OF SEQ ID NOS: 40

<210> SEQ ID NO 1
<211> LENGTH: 1710
<212> TYPE: DNA
<213> ORGANISM: Citrus sinensis

<400> SEQUENCE: 1

```
atgtatagtc ccactcccag tcccaggcga agaaccagac tcttacttgc tctcttaccc      60
agttcagcta tttcttgct actatttgta ctatcagctg taagtgtaac caccctcaaa      120
aagaacccca aaacaacaga tgccccacac ttgcgagtcc ataaacattt ccaggttgct      180
cattccgcat gcgaaggcac actctatcct gaactctgcg tttcgactct gctttcagtc      240
ccagatctcg cttcaaaaag agtccctgaa ctcatctccg taaccataaa ccgcacattg      300
tccgagctga gagcctcctc ctcaaactgc tccagcattg gacagagtta cccaaattt      360 aacacccttg aaaagagagc aatcaatgac tgtctcgagc tgtttcatga caccattgtt      420
gagctcaaat cagctctcaa tgatctctcc cccaagaaat cgccctccaa gcattaccat      480
gatttgcaaa ctttgtttag cggtgcaatg acaaaccagt acacgtgtct tgatgggttc      540
gcttacagtg acggaaacgt gagggaagtt attaagagca gcttgtacaa catttccagg      600
cacgtgagca actctttggt catgctcaag aaaatccccg tgataacat gtcttccaag      660 tacgaggttt ttcctgagta tgggcgtatt aagagaggat tcccaacttg gttgtcttta      720
aatgatcgca aattgttaca gaagtccgtt aatttgacca aatttgatct gatagtggct      780
aaagatggct ctgggaattt cactaccatt actgaagcag tggaagcagc tccaaacaaa      840
tccaatactc ggtttgtgat ttacataaaa gctggggctt atttgagaa cgtggaggtg      900 gataaaaaga agacaatgtt gatgttcgta ggagatggga tcggcaaaac attagtgaag      960
gccaatagaa gcgtcgttga tggatggact actttccggt cagccactgt agctgtggtg      1020
gggaccgggt ttatcgccaa aggcattaca gttgagaact cagctggtcc aagcaaacac      1080
caagcagtag ccttaaggag tggctcagat ctctcagctt tctacaaatg cagcttcgtt      1140
gggtaccaag acactctata tgttcattcc ctcagacaat tttatcgtga atgcgacgta      1200
tatggcacag ttgatttcat ctttggcaat gcagctgtgg tgttccaaat ctgcaactta      1260
tatgcccgta agccaaatgc aaaccaaaaa aatattatca ctgcacaggg gagagaagac      1320
cctaatcaaa atacagggat atcaatcttg aattgcaaag ttgctgctgc ttcggacttg      1380
```

-continued

```
attccatatc aaacagagtt taaaacatac cttggtcgtc cttggaaaga atattcgagg    1440
acggttttta tgctatctta tttgggcgat ttgatagcgc cggctggatg gttagaatgg    1500
aatggtacat ttgcattgag tacactcttt tacggggagt acaagaacag gggccctggt    1560
tctaacacga gtgccagagt gacgtggcct ggttacaggg tgatcaataa ctcggctgtg    1620
gcagctcaat ttacggccgg gccattcttg caaggaagtg aatggctaaa ttctactggc    1680
attcctttct atctcaattt gactccttga                                    1710
```

<210> SEQ ID NO 2
<211> LENGTH: 567
<212> TYPE: PRT
<213> ORGANISM: Citrus sinensis

<400> SEQUENCE: 2

```
Met Tyr Ser Pro Thr Pro Ser Pro Arg Arg Thr Arg Leu Leu Leu
1               5                  10                  15

Ala Leu Leu Pro Ser Ser Ala Ile Phe Leu Leu Phe Val Leu Ser
            20                  25                  30

Ala Val Ser Val Thr Thr Leu Lys Lys Asn Pro Lys Thr Thr Asp Ala
        35                  40                  45

Pro His Leu Arg Val His Lys His Phe Gln Val Ala His Ser Ala Cys
    50                  55                  60

Glu Gly Thr Leu Tyr Pro Glu Leu Cys Val Ser Thr Leu Leu Ser Val
65                  70                  75                  80

Pro Asp Leu Ala Ser Lys Arg Val Pro Glu Leu Ile Ser Val Thr Ile
                85                  90                  95

Asn Arg Thr Leu Ser Glu Leu Arg Ala Ser Ser Ser Asn Cys Ser Ser
            100                 105                 110

Ile Gly Gln Ser Tyr Pro Asn Phe Asn Thr Leu Glu Lys Arg Ala Ile
        115                 120                 125

Asn Asp Cys Leu Glu Leu Phe His Asp Thr Ile Val Glu Leu Lys Ser
    130                 135                 140

Ala Leu Asn Asp Leu Ser Pro Lys Lys Ser Pro Ser Lys His Tyr His
145                 150                 155                 160

Asp Leu Thr Leu Phe Ser Gly Ala Met Thr Asn Gln Tyr Thr Cys Leu
                165                 170                 175

Asp Gly Phe Ala Tyr Ser Asp Gly Asn Val Arg Glu Val Ile Lys Ser
            180                 185                 190

Ser Leu Tyr Asn Ile Ser Arg His Val Ser Asn Ser Leu Val Met Leu
        195                 200                 205

Lys Lys Ile Pro Gly Asp Asn Met Ser Ser Lys Tyr Glu Val Phe Pro
    210                 215                 220

Glu Tyr Gly Arg Ile Lys Arg Gly Phe Pro Thr Trp Leu Ser Leu Asn
225                 230                 235                 240

Asp Arg Lys Leu Leu Gln Lys Ser Val Asn Leu Thr Lys Phe Asp Leu
                245                 250                 255

Ile Val Ala Lys Asp Gly Ser Gly Asn Phe Thr Thr Ile Thr Glu Ala
            260                 265                 270

Val Glu Ala Ala Pro Asn Lys Ser Asn Thr Arg Phe Val Ile Tyr Ile
        275                 280                 285

Lys Ala Gly Ala Tyr Phe Glu Asn Val Glu Val Asp Lys Lys Lys Thr
    290                 295                 300

Met Leu Met Phe Val Gly Asp Gly Ile Gly Lys Thr Leu Val Lys Ala
305                 310                 315                 320
```

```
Asn Arg Ser Val Val Asp Gly Trp Thr Thr Phe Arg Ser Ala Thr Val
            325                 330                 335

Ala Val Val Gly Thr Gly Phe Ile Ala Lys Gly Ile Thr Val Glu Asn
            340                 345                 350

Ser Ala Gly Pro Ser Lys His Gln Ala Val Ala Leu Arg Ser Gly Ser
            355                 360                 365

Asp Leu Ser Ala Phe Tyr Lys Cys Ser Phe Val Gly Tyr Gln Asp Thr
            370                 375                 380

Leu Tyr Val His Ser Leu Arg Gln Phe Tyr Arg Glu Cys Asp Val Tyr
385                 390                 395                 400

Gly Thr Val Asp Phe Ile Phe Gly Asn Ala Ala Val Val Phe Gln Ile
            405                 410                 415

Cys Asn Leu Pro Asn Gln Asn Thr Gly Ile Ser Ile Tyr Ala Arg Lys
            420                 425                 430

Pro Asn Ala Asn Gln Lys Asn Ile Ile Thr Ala Gln Gly Arg Glu Asp
            435                 440                 445

Leu Asn Cys Lys Val Ala Ala Ala Ser Asp Leu Ile Pro Tyr Gln Thr
            450                 455                 460

Glu Phe Lys Thr Tyr Leu Gly Arg Pro Trp Lys Glu Tyr Ser Arg Thr
465                 470                 475                 480

Val Phe Met Leu Ser Tyr Leu Gly Asp Leu Ile Ala Pro Ala Gly Trp
            485                 490                 495

Leu Glu Trp Asn Gly Thr Phe Ala Leu Ser Thr Leu Phe Tyr Gly Glu
            500                 505                 510

Tyr Lys Asn Arg Gly Pro Gly Ser Asn Thr Ser Ala Arg Val Thr Trp
            515                 520                 525

Pro Gly Arg Val Ile Asn Asn Ser Ala Val Ala Ala Gln Phe Thr Ala
            530                 535                 540

Gly Pro Phe Leu Gln Gly Ser Glu Trp Leu Asn Ser Thr Gly Ile Pro
545                 550                 555                 560

Phe Tyr Leu Asn Leu Thr Pro
                565

<210> SEQ ID NO 3
<211> LENGTH: 18
<212> TYPE: PRT
<213> ORGANISM: Citrus sinensis
<220> FEATURE:
<221> NAME/KEY: misc_feature
<222> LOCATION: (6)..(6)
<223> OTHER INFORMATION: Xaa can be any naturally occurring amino acid

<400> SEQUENCE: 3

Leu Gln Lys Ser Val Xaa Leu Thr Lys Phe Asp Leu Ile Val Ala Val
1               5                   10                  15

Lys Asp

<210> SEQ ID NO 4
<211> LENGTH: 12
<212> TYPE: PRT
<213> ORGANISM: Citrus sinensis

<400> SEQUENCE: 4

Thr Met Leu Met Phe Val Gly Asp Gly Ile Gly Lys
1               5                   10

<210> SEQ ID NO 5
```

```
<211> LENGTH: 14
<212> TYPE: PRT
<213> ORGANISM: Citrus sinensis

<400> SEQUENCE: 5

Ser Ala Thr Val Ala Val Val Gly Thr Gly Phe Ile Ala Lys
1               5                   10

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 6
ccagcattgg acagagttac                                            20

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
aatcaacggt gccatatacg                                            20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
tcccatctcc tacgaacatc                                            20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
ttgatgggtt cgcttacagt                                            20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10
acgcttctat tggccttcac                                            20

<210> SEQ ID NO 11
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 11
```
ggcttatttt gagaacgtgg a                                              21

<210> SEQ ID NO 12
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 12
ggatcggcaa aacagtagtg a                                              21

<210> SEQ ID NO 13
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 13
tccctcacgt ttccgtcact gt                                             22

<210> SEQ ID NO 14
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 14
tcaccgggga ttttcttgag ca                                             22

<210> SEQ ID NO 15
<211> LENGTH: 11
<212> TYPE: PRT
<213> ORGANISM: Citrus sinensis

<400> SEQUENCE: 15

Lys Ala Tyr Phe Glu Asn Val Glu Val Ser Arg
1               5                   10

<210> SEQ ID NO 16
<211> LENGTH: 12
<212> TYPE: PRT
<213> ORGANISM: Citrus sinensis

<400> SEQUENCE: 16

Ala Gly Ala Tyr Phe Glu Asn Val Glu Val Asp Lys
1               5                   10

<210> SEQ ID NO 17
<211> LENGTH: 7
<212> TYPE: PRT
<213> ORGANISM: Citrus sinensis

<400> SEQUENCE: 17

His Gln Ala Val Ala Leu Arg
1               5

<210> SEQ ID NO 18
<211> LENGTH: 8
<212> TYPE: PRT
<213> ORGANISM: Citrus sinensis

<400> SEQUENCE: 18

```
Asn Ile Ile Thr Ala Gln Gly Arg
1               5

<210> SEQ ID NO 19
<211> LENGTH: 7
<212> TYPE: PRT
<213> ORGANISM: Citrus sinensis

<400> SEQUENCE: 19

Val Thr Trp Pro Gly Tyr Arg
1               5

<210> SEQ ID NO 20
<211> LENGTH: 8
<212> TYPE: PRT
<213> ORGANISM: Citrus sinensis

<400> SEQUENCE: 20

Thr Tyr Leu Gly Arg Pro Trp Lys
1               5

<210> SEQ ID NO 21
<211> LENGTH: 10
<212> TYPE: PRT
<213> ORGANISM: Citrus sinensis

<400> SEQUENCE: 21

Ser Gly Ser Asp Leu Ser Ala Phe Tyr Lys
1               5                   10

<210> SEQ ID NO 22
<211> LENGTH: 12
<212> TYPE: PRT
<213> ORGANISM: Citrus sinensis

<400> SEQUENCE: 22

Gly Ile Thr Val Glu Asn Ser Ala Gly Pro Ser Lys
1               5                   10

<210> SEQ ID NO 23
<211> LENGTH: 10
<212> TYPE: PRT
<213> ORGANISM: Citrus sinensis

<400> SEQUENCE: 23

Ser Val Val Asp Gly Trp Thr Thr Phe Arg
1               5                   10

<210> SEQ ID NO 24
<211> LENGTH: 15
<212> TYPE: PRT
<213> ORGANISM: Citrus sinensis

<400> SEQUENCE: 24

Val Ala Ala Ala Ser Asp Leu Leu Pro Tyr Gln Thr Glu Phe Lys
1               5                   10                  15

<210> SEQ ID NO 25
<211> LENGTH: 16
<212> TYPE: PRT
<213> ORGANISM: Citrus sinensis

<400> SEQUENCE: 25

Cys Ser Phe Val Gly Tyr Gln Asp Thr Leu Tyr Val His Ser Leu Arg
1               5                   10                  15
```

```
<210> SEQ ID NO 26
<211> LENGTH: 31
<212> TYPE: PRT
<213> ORGANISM: Citrus sinensis

<400> SEQUENCE: 26

Ser Ala Thr Val Ala Val Val Gly Thr Gly Phe Ile Ala Lys Gly Ile
1               5                   10                  15

Thr Val Glu Asn Ser Ala Gly Pro Ser Lys His Gln Ala Val Ala
            20                  25                  30

<210> SEQ ID NO 27
<211> LENGTH: 58
<212> TYPE: PRT
<213> ORGANISM: Citrus sinensis

<400> SEQUENCE: 27

Ser Ala Thr Val Ala Val Val Gly Thr Gly Phe Ile Ala Lys Gly Ile
1               5                   10                  15

Thr Val Glu Asn Ser Ala Gly Pro Ser Lys His Gln Ala Val Ala Leu
            20                  25                  30

Arg Ser Gly Ser Asp Leu Ser Ala Phe Tyr Lys Cys Ser Phe Val Gly
        35                  40                  45

Tyr Gln Asp Thr Leu Tyr Val His Ser Leu
    50                  55

<210> SEQ ID NO 28
<211> LENGTH: 41
<212> TYPE: PRT
<213> ORGANISM: Citrus Clementina

<400> SEQUENCE: 28

Ser Ala Thr Val Ala Val Val Gly Thr Gly Phe Ile Ala Lys Gly Ile
1               5                   10                  15

Thr Val Glu Asn Ser Ala Gly Pro Ser Lys His Gln Ala Val Ala Leu
            20                  25                  30

Arg Ser Gly Ser Asp Leu Ser Ala Phe
        35                  40

<210> SEQ ID NO 29
<211> LENGTH: 6
<212> TYPE: PRT
<213> ORGANISM: Citrus sinensis

<400> SEQUENCE: 29

Ser Val Asn Leu Thr Lys
1               5

<210> SEQ ID NO 30
<211> LENGTH: 7
<212> TYPE: PRT
<213> ORGANISM: Citrus sinensis

<400> SEQUENCE: 30

Phe Asp Leu Ile Val Ala Lys
1               5

<210> SEQ ID NO 31
<211> LENGTH: 19
<212> TYPE: PRT
<213> ORGANISM: Citrus sinensis
```

```
<400> SEQUENCE: 31

Asp Gly Ser Gly Asn Phe Thr Thr Ile Thr Glu Ala Val Glu Ala Ala
1               5                   10                  15

Pro Asn Lys

<210> SEQ ID NO 32
<211> LENGTH: 6
<212> TYPE: PRT
<213> ORGANISM: Citrus sinensis

<400> SEQUENCE: 32

Phe Val Ile Tyr Ile Lys
1               5

<210> SEQ ID NO 33
<211> LENGTH: 4
<212> TYPE: PRT
<213> ORGANISM: Citrus sinensis

<400> SEQUENCE: 33

Gln Phe Tyr Arg
1

<210> SEQ ID NO 34
<211> LENGTH: 27
<212> TYPE: PRT
<213> ORGANISM: Citrus sinensis

<400> SEQUENCE: 34

Glu Cys Asp Val Tyr Gly Thr Val Asp Phe Ile Phe Gly Asn Ala Ala
1               5                   10                  15

Val Val Phe Gln Ile Cys Asn Leu Tyr Ala Arg
            20                  25

<210> SEQ ID NO 35
<211> LENGTH: 7
<212> TYPE: PRT
<213> ORGANISM: Citrus sinensis

<400> SEQUENCE: 35

Lys Pro Asn Ala Asn Gln Lys
1               5

<210> SEQ ID NO 36
<211> LENGTH: 15
<212> TYPE: PRT
<213> ORGANISM: Citrus sinensis

<400> SEQUENCE: 36

Glu Asp Pro Asn Gln Asn Thr Gly Ile Ser Ile Leu Asn Cys Lys
1               5                   10                  15

<210> SEQ ID NO 37
<211> LENGTH: 4
<212> TYPE: PRT
<213> ORGANISM: Citrus sinensis

<400> SEQUENCE: 37

Glu Tyr Ser Arg
1

<210> SEQ ID NO 38
```

```
<211> LENGTH: 35
<212> TYPE: PRT
<213> ORGANISM: Citrus sinensis

<400> SEQUENCE: 38

Thr Val Phe Met Leu Ser Tyr Leu Gly Asp Leu Ile Ala Pro Ala Gly
1               5                   10                  15

Trp Leu Glu Trp Asn Gly Thr Phe Ala Leu Ser Thr Leu Phe Tyr Gly
            20                  25                  30

Glu Tyr Lys
        35

<210> SEQ ID NO 39
<211> LENGTH: 9
<212> TYPE: PRT
<213> ORGANISM: Citrus sinensis

<400> SEQUENCE: 39

Gly Pro Gly Ser Asn Thr Ser Ala Arg
1               5

<210> SEQ ID NO 40
<211> LENGTH: 36
<212> TYPE: PRT
<213> ORGANISM: Citrus sinensis

<400> SEQUENCE: 40

Val Ile Asn Asn Ser Ala Val Ala Ala Gln Gly Thr Ala Gly Pro Phe
1               5                   10                  15

Leu Gln Gly Ser Glu Trp Leu Asn Ser Thr Gly Ile Pro Phe Tyr Leu
            20                  25                  30

Asn Leu Thr Pro
        35
```